United States Patent [19]

Koblan et al.

[11] Patent Number: 5,474,921
[45] Date of Patent: Dec. 12, 1995

[54] EXPRESSION AND PURIFICATION OF PHOSPHOINOSITIDE-SPECIFIC PHOSPHOLIPASE C-γ

[75] Inventors: Kenneth S. Koblan, Chalfont; David L. Pompliano, Lansdale, both of Pa.

[73] Assignee: Merck & Co., Inc., Rahway, N.J.

[21] Appl. No.: 138,641

[22] Filed: Oct. 15, 1993

[51] Int. Cl.$^6$ .............. C12N 9/16; C12N 9/20; C12N 15/55; C07K 1/22
[52] U.S. Cl. .............. 435/196; 435/69.1; 435/199; 530/413
[58] Field of Search .............. 435/69.1, 196, 435/199, 252.3, 320.1; 530/413

[56] References Cited

U.S. PATENT DOCUMENTS

| | | | |
|---|---|---|---|
| 5,004,692 | 4/1991 | Tso et al. | 435/183 |
| 5,279,966 | 1/1994 | Jessell et al. | 435/69.1 |
| 5,376,367 | 12/1994 | Williams | 435/69.52 |

OTHER PUBLICATIONS

Homma et al "Tissue- and Cell Type-Specific Expression of mRNAS for Four Types of Inositol Phospholipid-Specific Phospholipase C", *BBRC* 164(1):406–412 (Oct. 1989).
Katan et al "Determination of the Primary Structure of PLC-154 . . ." *Cell* 54:171–177 (Jul. 1988).
Rhee et al "Studies of Inositol Phospholipid-Specific Phospholipase C" *Science* 244:546–550 (May 1989).
Ryu et al "Purification and Characterization of Two Immunologically Distinct . . ." *J. Biol. Chem.* 262(26):12511–12518 (Sep. 1987).
Suh et al "Monoclonal Antibodies to Three Phospholipase C Isozymes from Bovine Brain", *J. Biol. Chem.* 263(28):14497–14504 (Oct. 1988).
Rebecchi et al "Purification of a Phosphoinositide-specific Phospholipase C from Bovine Brain", *J. Biol. Chem.* 262(26):12526–12532 (Sep. 1987).
Bristol, A., et al., Phospholipase C-148: Chromosomal Location and Deletion Mapping of Functional Domains, (1988), Cold Spring Harbor Symposia on Quantitative Biology, vol. LIII, pp. 915–920.
Bonekamp, F., et al., The AGG codon is translated slowly in *E. coli* even at very low expression levels, (1988), Nucleic Acids Research, 16, pp. 3013–3024.
Burgess, W. H., et al., Characterization and cDNA Cloning of Phospholipase C-gamma, a Major Substrate for Heparin-Binding Growth Factor 1 (Acidic Fibroblast Growth Factor)-Activated Tyrosine Kinase, (1990), Mol. and Cellular Biol., 10, pp. 4770–4777.
Eisenberg, S. P., et al., Primary structure and functional expression from complementary DNA of a human interleukin-1 receptor antagonist, (1990), Nature, 343, pp. 341–346.
Crooke, S. T., et al., Mammalian phosphoinositide-specific phospholipase C isoenzymes, (1989), Cell Calcium, 10, pp. 309–323.
Emori, Y., et al., A Second Type of Rat Phosphoinositide-specific Phospholipase C Containing a src-related Sequence Not Essential for Phosphoinositide-hydrolyzing Activity*, (1989), The Jour. of Biol. Chem., 264, pp. 21885–21890.
Ginger, R. S., et al., Expression, purification and characterisation of a functional phosphatidylinositol-specific phospholipase C–delta 1 protein in *Escherichia coli*, (1992), Eur. J. Biochem., 210, pp. 155–160.
Katan, M., et al., Primary Structure of PLC-154, (1988), Cold Spring Harbor Symposia on Quantitative Biology, vol. LIII, pp. 921–926.
Kilmartin, J. V., Rat Monoclonal Antitubulin Antibodies Derived by Using a New Nonsecreting Rat Cell Line, (1982), The Jour. of Cell Biol., 93, pp. 576–582.
Rhee, S. G., et al., Assays of Phosphoinositide-Specific Phospholipase C and Purification of Isozymes from Bovine Brains, (1991), Methods in Enzymology, 197, pp. 502–511.
Sanger, F., et al., DNA sequencing with chain-terminating inhibitors, (1977), Proc. Natl. Acad. Sci., 74, pp. 5463–5467.
Stahl, M. L., et al., Sequence similarity of phospholipase C with the non-catalytic region of src, (1988), Nature, 332, pp. 269–272.
Suh, P-G., et al., Inositol phospholipid-specific phospholipase C: Complete cDNA and protein sequences and sequence homology to tyrosine kinase-related oncogene products, (1988), Prod. Natl. Acad. Sci., 85, pp. 5419–5423.

*Primary Examiner*—Stephen G. Walsh
*Attorney, Agent, or Firm*—David A. Muthard; Mark R. Daniel

[57] ABSTRACT

The present invention is directed to an assay which is used to determine the inhibitory activity of a test compound against a particular phosphoinositide-specific phospholipase C enzyme, that enzyme being phospholipase Cγ. The present invention is also directed to the preparation of phospholipase Cγ by recombinant expression in a bacterial cell and isolation of the expressed enzyme.

1 Claim, 11 Drawing Sheets

```
1/1                                    31/11
ATG GCG GGC GCC GCG TCC CCC TGC GCC AAC GGC TGC GGG CCC AGC GCG CCC TCC GAA GCG
Met ala gly ala ala ser pro cys ala asn gly cys gly pro ser ala pro ser glu ala
61/21                                  91/31
GAG GTG CTG CAC CTC TGC CGC AGC CTC GAG GTG GGC ACC GTC ATG ACT TTG TTC TAC TCC
glu val leu his leu cys arg ser leu glu val gly thr val met thr leu phe tyr ser
121/41                                 151/51
AAG AAG TCG CAG CGG CCA GAA CGG AAG ACC TTC CAG GTC AAG TTG GAG ACG CGC CAG ATC
lys lys ser gln arg pro glu arg lys thr phe gln val lys leu glu thr arg gln ile
181/61                                 211/71
ACA TGG AGC CGC GGT GCG GAC AAA ATC GAG GGG TCC ATC GAT ATC CGA GAA ATC AAG GAG
thr trp ser arg gly ala asp lys ile glu gly ser ile asp ile arg glu ile lys glu
241/81                                 271/91
ATC CGC CCA GGG AAG ACT TCC CGG GAC TTT GAC CGC TAC CAA GAA GAC CCT GCC TTC CGG
ile arg pro gly lys thr ser arg asp phe asp arg tyr gln glu asp pro ala phe arg
301/101                                331/111
CCA GAT CAG TCA CAC TGT TTT GTC ATC CTC TAT GGA ATG GAA TTC CGC CTG AAG ACC CTG
pro asp gln ser his cys phe val ile leu tyr gly met glu phe arg leu lys thr leu
361/121                                391/131
AGC CTG CAA GCC ACA TCT GAG GAT GAA GTG AAC ATG TGG ATC AAG GGC TTA ACT TGG CTC
ser leu gln ala thr ser glu asp glu val asn met trp ile lys gly leu thr trp leu
421/141                                451/151
ATG GAA GAT ACG CTG CAG GCG GCC ACA CCC CTG CAA ATT GAG AGA TGG CTC CGG AAG CAG
met glu asp thr leu gln ala ala thr pro leu gln ile glu arg trp leu arg lys gln
481/161                                511/171
TTC TAC TCA GTG GAT CGT AAC CGA GAG GAT CGT ATA TCA GCC AAG GAC CTG AAG AAC ATG
phe tyr ser val asp arg asn arg glu asp arg ile ser ala lys asp leu lys asn met
541/181                                571/191
CTG TCA CAG GTC AAC TAC CGG GTC CCC AAC ATG CGC TTC CTC CGA GAG CGG CTG ACG GAC
leu ser gln val asn tyr arg val pro asn met arg phe leu arg glu arg leu thr asp
601/201                                631/211
TTT GAA CAG CGC AGC GGG GAC ATC ACC TAT GGG CAG TTT GCT CAG CTT TAC CGC AGC CTC
phe glu gln arg ser gly asp ile thr tyr gly gln phe ala gln leu tyr arg ser leu
661/221                                691/231
ATG TAC AGC GCC CAG AAG ACG ATG GAC CTT CCG TTC TTG GAA ACC AAC ACT TTG AGG ACT
met tyr ser ala gln lys thr met asp leu pro phe leu glu thr asn thr leu arg thr
721/241                                751/251
GGA GAG CGG CCA GAG CTT TGC CAG GTG TCC CTT TCT GAG TTC CAG CAG TTC CTT CTT GAG
gly glu arg pro glu leu cys gln val ser leu ser glu phe gln gln phe leu leu glu
```

FIG.2A

781/261
TAC CAG GGG GAG CTG TGG GCT GTC GAC CGG
tyr gln gly glu leu trp ala val asp arg
811/271
CTT CAG GTG CAG GAA TTT ATG CTC AGC TTC
leu gln val gln glu phe met leu ser phe
841/281
CTT CGA GAC CCC TTG CGA GAG ATT GAG GAG
leu arg asp pro leu arg glu ile glu glu
871/291
CCA TAC TTC TTC TTG GAT GAG CTT GTC ACC
pro tyr phe phe leu asp glu leu val thr
901/301
TTT CTG TTC TCC AAA GAG AAC AGT GTG TGG
phe leu phe ser lys glu asn ser val trp
931/311
AAC TCA CAG CTG GAT GCC GTG TGC CCA GAA
asn ser gln leu asp ala val cys pro glu
961/321
ACC ATG AAC AAC CCA CTG TCT CAC TAT TGG
thr met asn asn pro leu ser his tyr trp
991/331
ATC TCT TCC TCG CAT AAT ACG TAT CTG ACT
ile ser ser ser his asn thr tyr leu thr
1021/341
GGG GAC CAG TTC TCC AGC GAG TCC TCC CTG
gly asp gln phe ser ser glu ser ser leu
1051/351
GAA GCC TAC GCT CGC TGC CTG AGG ATG GGC
glu ala tyr ala arg cys leu arg met gly
1081/361
TGT CGC TGC ATC GAG TTG GAC TGC TGG GAT
cys arg cys ile glu leu asp cys trp asp
1111/371
GGG CCA GAT GGG ATG CCA GTC ATT TAC CAT
gly pro asp gly met pro val ile tyr his
1141/381
GGG CAC ACC CTC ACC ACC AAG ATT AAG TTC
gly his thr leu thr thr lys ile lys phe
1171/391
TCA GAT GTC CTG CAC ACC ATC AAG GAG CAC
ser asp val leu his thr ile lys glu his
1201/401
GCG TTC GTA GCC TCA GAG TAC CCT GTC ATC
ala phe val ala ser glu tyr pro val ile
1231/411
CTG TCC ATC GAG GAC CAC TGC AGC ATT GCC
leu ser ile glu asp his cys ser ile ala
1261/421
CAG CAG AGG AAC ATG GCC CAG CAC TTC AGG
gln gln arg asn met ala gln his phe arg
1291/431
AAG GTG CTC GGT GAC ACG CTC CTC ACC AAG
lys val leu gly asp thr leu leu thr lys
1321/441
CCC GTG GAC ATT GCC GCT GAT GGG CTC CCT
pro val asp ile ala ala asp gly leu pro
1351/451
TCT CCC AAC CAG CTC AAG AGG AAG ATC CTG
ser pro asn gln leu lys arg lys ile leu
1381/461
ATT AAG CAT AAG AAG CTG GCT GAG GGC AGT
ile lys his lys lys leu ala glu gly ser
1411/471
GCC TAT GAG GAG GTG CCT ACC TCT GTG ATG
ala tyr glu glu val pro thr ser val met
1441/481
TAC TCT GAG AAT GAC ATC AGT AAC TCC ATC
tyr ser glu asn asp ile ser asn ser ile
1471/491
AAG AAT GGT ATC CTC TAC TTG GAG GAC CCC
lys asn gly ile leu tyr leu glu asp pro
1501/501
GTG AAT CAT GAG TGG TAC CCC CAC TAC TTT
val asn his glu trp tyr pro his tyr phe
1531/511
GTT CTG ACT AGC AGC AAG ATC TAC TAC TCT
val leu thr ser ser lys ile tyr tyr ser

FIG.2B

1561/521
GAG GAG ACC AGC AGT GAC CAG GGA AAT GAG GAT GAA GAG GAG CCG AAG GAG GCC AGT GGC
glu glu thr ser ser asp gln gly asn glu asp glu glu glu pro lys glu ala ser gly
1621/541                                               1651/551
AGC ACA GAG CTG CAC TCG AGC GAG AAG TGG TTC CAC GGG AAG CTC GGG GCT GGG CGC GAC
ser thr glu leu his ser ser glu lys trp phe his gly lys leu gly ala gly arg asp
1681/561                                               1711/571
GGG CGG CAC ATT GCT GAG CGC CTG CTC ACC GAG TAC TGC ATA GAG ACT GGG GCT CCC GAT
gly arg his ile ala glu arg leu leu thr glu tyr cys ile glu thr gly ala pro asp
1741/581                                               1771/591
GGC TCC TTC CTA GTG CGA GAA AGT GAG ACC TTC GTG GGG GAC TAC ACG CTG TCT TTT TGG
gly ser phe leu val arg glu ser glu thr phe val gly asp tyr thr leu ser phe trp
1801/601                                               1831/611
CGG AAT GGG AAA GTC CAG CAC TGC CGT ATC CAC TCC CGG CAG GAT GCT GGG ACT CCT AAG
arg asn gly lys val gln his cys arg ile his ser arg gln asp ala gly thr pro lys
1861/621                                               1891/631
TTC TTC TTG ACA GAT AAC CTT GTC TTT GAC TCT CTC TAT GAC CTC ATC ACA CAT TAT CAG
phe phe leu thr asp asn leu val phe asp ser leu tyr asp leu ile thr his tyr gln
1921/641                                               1951/651
CAA GTG CCC CTG CGC TGC AAT GAG TTT GAG ATG CGC CTT TCA GAG CCT GTT CCA CAG ACG
gln val pro leu arg cys asn glu phe glu met arg leu ser glu pro val pro gln thr
1981/661                                               2011/671
AAT GCC CAT GAG AGC AAA GAG TGG TAC CAC GCA AGC CTG ACT AGA GCT CAG GCT GAA CAC
asn ala his glu ser lys glu trp tyr his ala ser leu thr arg ala gln ala glu his
2041/681                                               2071/691
ATG CTG ATG CGA GTA CCC CGT GAT GGG GCC TTC CTG GTG CGG AAG CGC AAC GAG CCC AAC
met leu met arg val pro arg asp gly ala phe leu val arg lys arg asn glu pro asn
2101/701                                               2131/711
TCC TAT GCC ATC TCT TTC CGG GCT GAG GGA AAG ATC AAG CAC TGC CGA GTA CAG CAG GAA
ser tyr ala ile ser phe arg ala glu gly lys ile lys his cys arg val gln gln glu
2161/721                                               2191/731
GGC CAG ACT GTG ATG CTG GGG AAC TCT GAG TTT GAC AGC CTG GTC GAC CTC ATC AGC TAC
gly gln thr val met leu gly asn ser glu phe asp ser leu val asp leu ile ser tyr
2221/741                                               2251/751
TAT GAG AAG CAT CCC CTG TAC CGC AAA ATG AAA CTG CGC TAC CCC ATC AAC GAG GAG GCG
tyr glu lys his pro leu tyr arg lys met lys leu arg tyr pro ile asn glu glu ala
2281/761                                               2311/771
CTG GAG AAG ATT GGG ACA GCT GAA CCC GAT TAT GGG GCA CTG TAT GAG GGC CGC AAC CCT
leu glu lys ile gly thr ala glu pro asp tyr gly ala leu tyr glu gly arg asn pro

FIG.2C

2341/781
GGT TTC TAT GTG GAG GCC AAC CCT ATG CCA
gly phe tyr val glu ala asn pro met pro
2371/791
ACT TTC AAG TGT GCA GTA AAA GCT CTC TTC
thr phe lys cys ala val lys ala leu phe 2401/801
GAC TAC AAG GCC CAG AGA GAG GAT GAG CTG
asp tyr lys ala gln arg glu asp glu leu
2431/811
ACT TTT ACC AAG AGC GCC ATC ATC CAG AAT
thr phe thr lys ser ala ile ile gln asn 2461/821
GTG GAA AAG CAA GAT GGT GGC TGG TGG CGT
val glu lys gln asp gly gly trp trp arg
2491/831
GGG GAC TAT GGT GGG AAG AAG CAG CTG TGG
gly asp tyr gly gly lys lys gln leu trp 2521/841
TTC CCC TCA AAC TAT GTG GAA GAG ATG ATC
phe pro ser asn tyr val glu glu met ile
2551/851
AAT CCA GCA ATC CTA GAG CCG GAG AGG GAG
asn pro ala ile leu glu pro glu arg glu 2581/861
CAT CTG GAT GAG AAC AGC CCA CTG GGG GAC
his leu asp glu asn ser pro leu gly asp
2611/871
TTG CTG CGA GGG GTC TTA GAT GTG CCA GCC
leu leu arg gly val leu asp val pro ala 2641/881
TGC CAG ATC GCC ATT CGT CCT GAG GGC AAA
cys gln ile ala ile arg pro glu gly lys
2671/891
AAC AAC CGG CTC TTC GTC TTC TCC ATC AGC
asn asn arg leu phe val phe ser ile ser 2701/901
ATG CCG TCA GTG GCT CAG TGG TCC CTA GAC
met pro ser val ala gln trp ser leu asp
2731/911
GTT GCC GCT GAC TCA CAG GAG GAG TTG CAG
val ala ala asp ser gln glu glu leu gln 2761/921
GAC TGG GTG AAA AAG ATC CGT GAA GTT GCC
asp trp val lys lys ile arg glu val ala
2791/931
CAG ACT GCA GAT GCC AGG CTT ACT GAG GGG
gln thr ala asp ala arg leu thr glu gly 2821/941
AAG ATG ATG GAG CGG CGG AAG AAG ATC GCC
lys met met glu arg arg lys lys ile ala
2851/951
TTG GAG CTC TCC GAG CTC GTG GTC TAC TGC
leu glu leu ser glu leu val val tyr cys 2881/961
CGG CCT GTT CCC TTT GAC GAA GAG AAG ATT
arg pro val pro phe asp glu glu lys ile
2911/971
GGC ACA GAA CGC GCT TGT TAC CGG GAC ATG
gly thr glu arg ala cys tyr arg asp met 2941/981
TCC TCC TTT CCG GAA ACC AAG GCT GAG AAG
ser ser phe pro glu thr lys ala glu lys
2971/991
TAT GTG AAC AAG GCC AAA GGC AAG AAG TTC
tyr val asn lys ala lys gly lys lys phe 3001/1001
CTC CAG TAC AAC CGG CTG CAG CTC TCT CGC
leu gln tyr asn arg leu gln leu ser arg
3031/1011
ATC TAC CCT AAG GGT CAG AGG CTG GAC TCC
ile tyr pro lys gly gln arg leu asp ser 3061/1021
TCC AAT TAT GAC CCT CTG CCC ATG TGG ATC
ser asn tyr asp pro leu pro met trp ile
3091/1031
TGT GGC AGC CAG CTT GTA GCT CTC AAT TTT
cys gly ser gln leu val ala leu asn phe

FIG.2D

```
3121/1041                                   3151/1051
CAG ACC CCA GAC AAG CCT ATG CAG ATG AAC CAG GCC CTC TTC ATG GCT GGT GGA CAC TGT
gln thr pro asp lys pro met gln met asn gln ala leu phe met ala gly gly his cys
3181/1061                                   3211/1071
GGC TAT GTG CTG CAG CCA AGC ACC ATG AGA GAT GAA GCC TTT GAC CCC TTT GAT AAG AGC
gly tyr val leu gln pro ser thr met arg asp glu ala phe asp pro phe asp lys ser
3241/1081                                   3271/1091
AGT CTC CGA GGT CTG GAG CCC TGT GTC ATT TGC ATT GAG GTG CTG GGG GCC AGG CAT CTG
ser leu arg gly leu glu pro cys val ile cys ile glu val leu gly ala arg his leu
3301/1101                                   3331/1111
CCG AAG AAT GGC CGG GGT ATT GTG TGT CCT TTC GTG GAG ATT GAA GTG GCT GGG GCA GAG
pro lys asn gly arg gly ile val cys pro phe val glu ile glu val ala gly ala glu
3361/1121                                   3391/1131
TAC GAC AGC ACC AAG CAG AAG ACA GAG TTT GTA GTG GAC AAT GGA CTG AAC CCT GTG TGG
tyr asp ser thr lys gln lys thr glu phe val val asp asn gly leu asn pro val trp
3421/1141                                   3451/1151
CCT GCA AAG CCC TTC CAC TTC CAG ATC AGT AAC CCA GAG TTT GCC TTT CTG CGC TTT GTG
pro ala lys pro phe his phe gln ile ser asn pro glu phe ala phe leu arg phe val
3481/1161                                   3511/1171
GTG TAT GAG GAA GAC ATG TTT AGT GAC CAG AAC TTC TTG GCT CAG GCT ACT TTC CCA GTA
val tyr glu glu asp met phe ser asp gln asn phe leu ala gln ala thr phe pro val
3541/1181                                   3571/1191
AAA GGC CTG AAG ACA GGA TAC AGA GCA GTG CCT TTG AAG AAC AAC TAC AGT GAA GAC CTG
lys gly leu lys thr gly tyr arg ala val pro leu lys asn asn tyr ser glu asp leu
3601/1201                                   3631/1211
GAG TTG GCC TCC CTG CTC ATC AAG ATT GAC ATT TTC CCT GCT AAG GAG AAT GGT GAC CTC
glu leu ala ser leu leu ile lys ile asp ile phe pro ala lys glu asn gly asp leu
3661/1221                                   3691/1231
AGC CCT TTC AGT GGT ACA TCC CTA AGG GAA CGG GCC TCA GAT GCC TCC AGC CAG CTG TTC
ser pro phe ser gly thr ser leu arg glu arg ala ser asp ala ser ser gln leu phe
3721/1241                                   3751/1251
CAT GTC CGG GCC CGG GAA GGG TCC TTT GAA GCC AGA TAC CAG CAG CCA TTT GAA GAC TTC
his val arg ala arg glu gly ser phe glu ala arg tyr gln gln pro phe glu asp phe
3781/1261                                   3811/1271
CGC ATC TCG CAG GAG CAT CTC GCA GAC CAT TTT GAC AGT CGG GAA CGA AGG GCC CCA AGA
arg ile ser gln glu his leu ala asp his phe asp ser arg glu arg arg ala pro arg
3841/1281
AGG ACT CGG GTC AAT GGA GAC AAC CGC CTC
arg thr arg val asn gly asp asn arg leu
```

FIG.2E

```
1/1                                   31/11
ATG GCG GGC GCC GCG TCC CCC TGC GCC AAC GGC TGC GGG CCC AGC GCG CCC TCC GAA GCG
Met ala gly ala ala ser pro cys ala asn gly cys gly pro ser ala pro ser glu ala
61/21                                 91/31
GAG GTG CTG CAC CTC TGC CGC AGC CTC GAG GTG GGC ACC GTC ATG ACT TTG TTC TAC TCC
glu val leu his leu cys arg ser leu glu val gly thr val met thr leu phe tyr ser
121/41                                151/51
AAG AAG TCG CAG CGG CCA GAA CGG AAG ACC TTC CAG GTC AAG TTG GAG ACG CGC CAG ATC
lys lys ser gln arg pro glu arg lys thr phe gln val lys leu glu thr arg gln ile
181/61                                211/71
ACA TGG AGC CGC GGT GCG GAC AAA ATC GAG GGG TCC ATC GAT ATC CGA GAA ATC AAG GAG
thr trp ser arg gly ala asp lys ile glu gly ser ile asp ile arg glu ile lys glu
241/81                                271/91
ATC CGC CCA GGG AAG ACT TCC CGG GAC TTT GAC CGC TAC CAA GAA GAC CCT GCC TTC CGG
ile arg pro gly lys thr ser arg asp phe asp arg tyr gln glu asp pro ala phe arg
301/101                               331/111
CCA GAT CAG TCA CAC TGT TTT GTC ATC CTC TAT GGA ATG GAA TTC CGC CTG AAG ACC CTG
pro asp gln ser his cys phe val ile leu tyr gly met glu phe arg leu lys thr leu
361/121                               391/131
AGC CTG CAA GCC ACA TCT GAG GAT GAA GTG AAC ATG TGG ATC AAG GGC TTA ACT TGG CTC
ser leu gln ala thr ser glu asp glu val asn met trp ile lys gly leu thr trp leu
421/141                               451/151
ATG GAA GAT ACG CTG CAG GCG GCC ACA CCC CTG CAA ATT GAG AGA TGG CTC CGG AAG CAG
met glu asp thr leu gln ala ala thr pro leu gln ile glu arg trp leu arg lys gln
481/161                               511/171
TTC TAC TCA GTG GAT CGT AAC CGA GAG GAT CGT ATA TCA GCC AAG GAC CTG AAG AAC ATG
phe tyr ser val asp arg asn arg glu asp arg ile ser ala lys asp leu lys asn met
541/181                               571/191
CTG TCA CAG GTC AAC TAC CGG GTC CCC AAC ATG CGC TTC CTC GGA GAG CGG CTG ACG GAC
leu ser gln val asn tyr arg val pro asn met arg phe leu arg glu arg leu thr asp
601/201                               631/211
TTT GAA CAG CGC AGC GGG GAC ATC ACC TAT GGG CAG TTT GCT CAG CTT TAC CGC AGC CTC
phe glu gln arg ser gly asp ile thr tyr gly gln phe ala gln leu tyr arg ser leu
661/221                               691/231
ATG TAC AGC GCC CAG AAG ACG ATG GAC CTT CCG TTC TTG GAA ACC AAC ACT TTG AGG ACT
met tyr ser ala gln lys thr met asp leu pro phe leu glu thr asn thr leu arg thr
721/241                               751/251
GGA GAG CGG CCA GAG CTT TGC CAG GTG TCC CTT TCT GAG TTC CAG CAG TTC CTT CTT GAG
gly glu arg pro glu leu cys gln val ser leu ser glu phe gln gln phe leu leu glu
```

FIG.3A

```
781/261                           811/271
TAC CAG GGG GAG CTG TGG GCT GTC GAC CGG CTT CAG GTG CAG GAA TTT ATG CTC AGC TTC
tyr gln gly glu leu trp ala val asp arg leu gln val gln glu phe met leu ser phe
841/281                           871/291
CTT CGA GAC CCC TTG CGA GAG ATT GAG GAG CCA TAC TTC TTC TTG GAT GAG CTT GTC ACC
leu arg asp pro leu arg glu ile glu glu pro tyr phe phe leu asp glu leu val thr
901/301                           931/311
TTT CTG TTC TCC AAA GAG AAC AGT GTG TGG AAC TCA CAG CTG GAT GCC GTG TGC CCA GAA
phe leu phe ser lys glu asn ser val trp asn ser gln leu asp ala val cys pro glu
961/321                           991/331
ACC ATG AAC AAC CCA CTG TCT CAC TAT TGG ATC TCT TCC TCG CAT AAT ACG TAT CTG ACT
thr met asn asn pro leu ser his tyr trp ile ser ser ser his asn thr tyr leu thr
1021/341                          1051/351
GGG GAC CAG TTC TCC AGC GAG TCC TCC CTG GAA GCC TAC GCT CGC TGC CTG AGG ATG GGC
gly asp gln phe ser ser glu ser ser leu glu ala tyr ala arg cys leu arg met gly
1081/361                          1111/371
TGT CGC TGC ATC CAG TTG GAC TGC TGG GAT GGG CCA GAT GGG ATG CCA GTC ATT TAC CAT
cys arg cys ile gln leu asp cys trp asp gly pro asp gly met pro val ile tyr his
1141/381                          1171/391
GGG CAC ACC CTC ACC ACC AAG ATT AAG TTC TCA GAT GTC CTG CAC ACC ATC AAG GAG CAC
gly his thr leu thr thr lys ile lys phe ser asp val leu his thr ile lys glu his
1201/401                          1231/411
GCG TTC GTA GCC TCA GAG TAC CCT GTC ATC CTG TCC ATC GAG GAC CAC TGC AGC ATT GCC
ala phe val ala ser glu tyr pro val ile leu ser ile glu asp his cys ser ile ala
1261/421                          1291/431
CAG CAG AGG AAC ATG GCC CAG CAC TTC AGG AAG GTG CTC GGT GAC ACG CTC CTC ACC AAG
gln gln arg asn met ala gln his phe arg lys val leu gly asp thr leu leu thr lys
1321/441                          1351/451
CCC GTG GAC ATT GCC GCT GAT GGG CTC CCT TCT CCC AAC CAG CTC AAG AGG AAG ATC CTG
pro val asp ile ala ala asp gly leu pro ser pro asn gln leu lys arg lys ile leu
1381/461                          1411/471
ATT AAG CAT AAG AAG CTG GCT GAG GGC AGT GCC TAT GAG GAG GTG CCT ACC TCT GTG ATG
ile lys his lys lys leu ala glu gly ser ala tyr glu glu val pro thr ser val met
1441/481                          1471/491
TAC TCT GAG AAT GAC ATC AGT AAC TCC ATC AAG AAT GGT ATC CTC TAC TTG GAG GAC CCC
tyr ser glu asn asp ile ser asn ser ile lys asn gly ile leu tyr leu glu asp pro
1501/501                          1531/511
GTG AAT CAT GAG TGG TAC CCC CAC TAC TTT GTT CTG ACT AGC AGC AAG ATC TAC TAC TCT
val asn his glu trp tyr pro his tyr phe val leu thr ser ser lys ile tyr tyr ser
```

FIG.3B

```
1561/521                                    1591/531
GAG GAG ACC AGC AGT GAC CAG GGA AAT GAG GAT GAA GAG GAG CCG AAG GAG GCC AGT GGC
glu glu thr ser ser asp gln gly asn glu asp glu glu glu pro lys glu ala ser gly
1621/541                                    1651/551
AGC ACA GAG CTG CAC TCG AGC GAG AAG TGG TTC CAC GGG AAG CTC GGG GCT GGG CGC GAC
ser thr glu leu his ser ser glu lys trp phe his gly lys leu gly ala gly arg asp
1681/561                                    1711/571
GGG CGG CAC ATT GCT GAG CGC CTG CTC ACC GAG TAC TGC ATA GAG ACT GGG GCT CCC GAT
gly arg his ile ala glu arg leu leu thr glu tyr cys ile glu thr gly ala pro asp
1741/581                                    1771/591
GGC TCC TTC CTA GTG CGA GAA AGT GAG ACC TTC GTG GGG GAC TAC ACG CTG TCT TTT TGG
gly ser phe leu val arg glu ser glu thr phe val gly asp tyr thr leu ser phe trp
1801/601                                    1831/611
CGG AAT GGG AAA GTC CAG CAC TGC CGT ATC CAC TCC CGG CAG GAT GCT GGG ACT CCT AAG
arg asn gly lys val gln his cys arg ile his ser arg gln asp ala gly thr pro lys
1861/621                                    1891/631
TTC TTC TTG ACA GAT AAC CTT GTC TTT GAC TCT CTC TAT GAC CTC ATC ACA CAT TAT CAG
phe phe leu thr asp asn leu val phe asp ser leu tyr asp leu ile thr his tyr gln
1921/641                                    1951/651
CAA GTG CCC CTG CGC TGC AAT GAG TTT GAG ATG CGC CTT TCA GAG CCT GTT CCA CAG ACG
gln val pro leu arg cys asn glu phe glu met arg leu ser glu pro val pro gln thr
1981/661                                    2011/671
AAT GCC CAT GAG AGC AAA GAG TGG TAC CAC GCA AGC CTG ACT AGA GCT CAG GCT GAA CAC
asn ala his glu ser lys glu trp tyr his ala ser leu thr arg ala gln ala glu his
2041/681                                    2071/691
ATG CTG ATG CGA GTA CCC CGT GAT GGG GCC TTC CTG GTG CGG AAG CGC AAC GAG CCC AAC
met leu met arg val pro arg asp gly ala phe leu val arg lys arg asn glu pro asn
2101/701                                    2131/711
TCC TAT GCC ATC TCT TTC CGG GCT GAG GGA AAG ATC AAG CAC TGC CGA GTA CAG CAG GAA
ser tyr ala ile ser phe arg ala glu gly lys ile lys his cys arg val gln gln glu
2161/721                                    2191/731
GGC CAG ACT GTG ATG CTG GGG AAC TCT GAG TTT GAC AGC CTG GTC GAC CTC ATC AGC TAC
gly gln thr val met leu gly asn ser glu phe asp ser leu val asp leu ile ser tyr
2221/741                                    2251/751
TAT GAG AAG CAT CCC CTG TAC CGC AAA ATG AAA CTG CGC TAC CCC ATC AAC GAG GAG GCG
tyr glu lys his pro leu tyr arg lys met lys leu arg tyr pro ile asn glu glu ala
2281/761                                    2311/771
CTG GAG AAG ATT GGG ACA GCT GAA CCC GAT TAT GGG GCA CTG TAT GAG GGC CGC AAC CCT
leu glu lys ile gly thr ala glu pro asp tyr gly ala leu tyr glu gly arg asn pro
```

FIG.3C

2341/781
GGT TTC TAT GTG GAG GCC AAC CCT ATG CCA 2371/791 ACT TTC AAG TGT GCA GTA AAA GCT CTC TTC
gly phe tyr val glu ala asn pro met pro thr phe lys cys ala val lys ala leu phe
2401/801
GAC TAC AAG GCC CAG AGA GAG GAT GAG CTG 2431/811 ACT TTT ACC AAG AGC GCC ATC ATC CAG AAT
asp tyr lys ala gln arg glu asp glu leu thr phe thr lys ser ala ile ile gln asn
2461/821
GTG GAA AAG CAA GAT GGT GGC TGG TGG CGT 2491/831 GGG GAC TAT GGT GGG AAG AAG CAG CTG TGG
val glu lys gln asp gly gly trp trp arg gly asp tyr gly gly lys lys gln leu trp
2521/841
TTC CCC TCA AAC TAT GTG GAA GAG ATG ATC 2551/851 AAT CCA GCA ATC CTA GAG CCG GAG AGG GAG
phe pro ser asn tyr val glu glu met ile asn pro ala ile leu glu pro glu arg glu
2581/861
CAT CTG GAT GAG AAC AGC CCA CTG GGG GAC 2611/871 TTG CTG CGA GGG GTC TTA GAT GTG CCA GCC
his leu asp glu asn ser pro leu gly asp leu leu arg gly val leu asp val pro ala
2641/881
TGC CAG ATC GCC ATT CGT CCT GAG GGC AAA 2671/891 AAC AAC CGG CTC TTC GTC TTC TCC ATC AGC
cys gln ile ala ile arg pro glu gly lys asn asn arg leu phe val phe ser ile ser
2701/901
ATG CCG TCA GTG GCT CAG TGG TCC CTA GAC 2731/911 GTT GCC GCT GAC TCA CAG GAG GAG TTG CAG
met pro ser val ala gln trp ser leu asp val ala ala asp ser gln glu glu leu gln
2761/921
GAC TGG GTG AAA AAG ATC CGT GAA GTT GCC 2791/931 CAG ACT GCA GAT GCC AGG CTT ACT GAG GGG
asp trp val lys lys ile arg glu val ala gln thr ala asp ala arg leu thr glu gly
2821/941
AAG ATG ATG GAG cGG cGG AAG AAG ATC GCC 2851/951 TTG GAG CTC TCC GAG CTC GTG GTC TAC TGC
lys met met glu arg arg lys lys ile ala leu glu leu ser glu leu val val tyr cys
2881/961
CGG CCT GTT CCC TTT GAC GAA GAG AAG ATT 2911/971 GGC ACA GAA CGC GCT TGT TAC CGG GAC ATG
arg pro val pro phe asp glu glu lys ile gly thr glu arg ala cys tyr arg asp met
2941/981
TCC TCC TTT CCG GAA ACC AAG GCT GAG AAG 2971/991 TAT GTG AAC AAG GCC AAA GGC AAG AAG TTC
ser ser phe pro glu thr lys ala glu lys tyr val asn lys ala lys gly lys lys phe
3001/1001
CTC CAG TAC AAC CGG CTG CAG CTC TCT CGC 3031/1011 ATC TAC CCT AAG GGT CAG AGG CTG GAC TCC
leu gln tyr asn arg leu gln leu ser arg ile tyr pro lys gly gln arg leu asp ser
3061/1021
TCC AAT TAT GAC CCT CTG CCC ATG TGG ATC 3091/1031 TGT GGC AGC CAG CTT GTA GCT CTC AAT TTT
ser asn tyr asp por leu pro met trp ile cys gly ser gln leu val ala leu asn phe

FIG.3D

```
3121/1041                              3151/1051
CAG ACC CCA GAC AAG CCT ATG CAG ATG AAC CAG GCC CTC TTC ATG GCT GGT GGA CAC TGT
gln thr pro asp lys pro met gln met asn gln ala leu phe met ala gly gly his cys
3181/1061                              3211/1071
GGC TAT GTG CTG CAG CCA AGC ACC ATG AGA GAT GAA GCC TTT GAC CCC TTT GAT AAG AGC
gly tyr val leu gln pro ser thr met arg asp glu ala phe asp pro phe asp lys ser
3241/1081                              3271/1091
AGT CTC CGA GGT CTG GAG CCC TGT GTC ATT TGC ATT GAG GTG CTG GGG GCC AGG CAT CTG
ser leu arg gly leu glu pro cys val ile cys ile glu val leu gly ala arg his leu
3301/1101                              3331/1111
CCG AAG AAT GGC CGG GGT ATT GTG TGT CCT TTC GTG GAG ATT GAA GTG GCT GGG GCA GAG
pro lys asn gly arg gly ile val cys pro phe val glu ile glu val ala gly ala glu
3361/1121                              3391/1131
TAC GAC AGC ACC AAG CAG AAG ACA GAG TTT GTA GTG GAC AAT GGA CTG AAC CCT GTG TGG
tyr asp ser thr lys gln lys thr glu phe val val asp asn gly leu asn pro val trp
3421/1141                              3451/1151
CCT GCA AAG CCC TTC CAC TTC CAG ATC AGT AAC CCA GAG TTT GCC TTT CTG CGC TTT GTG
pro ala lys pro phe his phe gln ile ser asn pro glu phe ala phe leu arg phe val
3481/1161                              3511/1171
GTG TAT GAG GAA GAC ATG TTT AGT GAC CAG AAC TTC TTG GCT CAG GCT ACT TTC CCA GTA
val tyr glu glu asp met phe ser asp gln asn phe leu ala gln ala thr phe pro val
3541/1181                              3571/1191
AAA GGC CTG AAG ACA GGA TAC AGA GCA GTG CCT TTG AAG AAC AAC TAC AGT GAA GAC CTG
lys gly leu lys thr gly tyr arg ala val pro leu lys asn asn tyr ser glu asp leu
3601/1201                              3631/1211
GAG TTG GCC TCC CTG CTC ATC AAG ATT GAC ATT TTC CCT GCT AAG GAG AAT GGT GAC CTC
glu leu ala ser leu leu ile lys ile asp ile phe pro ala lys glu asn gly asp leu
3661/1221                              3691/1231
AGC CCT TTC AGT GGT ACA TCC CTA AGG GAA CGG GCC TCA GAT GCC TCC AGC CAG CTG TTC
ser pro phe ser gly thr ser leu arg glu arg ala ser asp ala ser ser gln leu phe
3721/1241                              3751/1251
CAT GTC CGG GCC CGG GAA GGG TCC TTT GAA GCC AGA TAC CAG CAG CCA TTT GAA GAC TTC
his val arg ala arg glu gly ser phe glu ala arg tyr gln gln pro phe glu asp phe
3781/1261                              3811/1271
CGC ATC TCG CAG GAG CAT CTC GCA GAC CAT TTT GAC AGT CGG GAA CGA AGG GCC CCA AGA
arg ile ser gln glu his leu ala asp his phe asp ser arg glu arg arg ala pro arg
3841/1281                              3871/1291
AGG ACT CGG GTC AAT GGA GAC AAC CGC CTC gaa gaa ttt TAG tct agA AGC TT
arg thr arg val asn gly asp asn arg leu glu glu phe AMB
```

FIG.3E

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
  ( A ) LENGTH: 3870 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:1:

```
ATGGCGGGCG  CCGCGTCCCC  CTGCGCCAAC  GGCTGCGGGC  CCAGCGCGCC  CTCCGAAGCG      60
GAGGTGCTGC  ACCTCTGCCG  CAGCCTCGAG  GTGGGCACCG  TCATGACTTT  GTTCTACTCC     120
AAGAAGTCGC  AGCGGCCAGA  ACGGAAGACC  TTCCAGGTCA  AGTTGGAGAC  GCGCCAGATC     180
ACATGGAGCC  GCGGTGCGGA  CAAAATCGAG  GGGTCCATCG  ATATCCGAGA  AATCAAGGAG     240
ATCCGCCCAG  GGAAGACTTC  CCGGGACTTT  GACCGCTACC  AAGAAGACCC  TGCCTTCCGG     300
CCAGATCAGT  CACACTGTTT  TGTCATCCTC  TATGGAATGG  AATTCCGCCT  GAAGACCCTG     360
AGCCTGCAAG  CCACATCTGA  GGATGAAGTG  AACATGTGGA  TCAAGGGCTT  AACTTGGCTC     420
ATGGAAGATA  CGCTGCAGGC  GGCCACACCC  TGCAAATTG   AGAGATGGCT  CCGGAAGCAG     480
TTCTACTCAG  TGGATCGTAA  CCGAGAGGAT  CGTATATCAG  CCAAGGACCT  GAAGAACATG     540
CTGTCACAGG  TCAACTACCG  GGTCCCCAAC  ATGCGCTTCC  TCCGAGAGCG  GCTGACGGAC     600
TTTGAACAGC  GCAGCGGGGA  CATCACCTAT  GGGCAGTTTG  CTCAGCTTTA  CCGCAGCCTC     660
ATGTACAGCG  CCCAGAAGAC  GATGGACCTT  CCGTTCTTGG  AAACCAACAC  TTTGAGGACT     720
GGAGAGCGGC  CAGAGCTTTG  CCAGGTGTCC  CTTTCTGAGT  TCCAGCAGTT  CCTTCTTGAG     780
TACCAGGGGG  AGCTGTGGGC  TGTCGACCGG  CTTCAGGTGC  AGGAATTTAT  GCTCAGCTTC     840
CTTCGAGACC  CCTTGCGAGA  GATTGAGGAG  CCATACTTCT  TCTTGGATGA  GCTTGTCACC     900
TTTCTGTTCT  CCAAAGAGAA  CAGTGTGTGG  AACTCACAGC  TGGATGCCGT  GTGCCCAGAA     960
ACCATGAACA  ACCCACTGTC  TCACTATTGG  ATCTCTTCCT  CGCATAATAC  GTATCTGACT    1020
GGGGACCAGT  TCTCCAGCGA  GTCCTCCCTG  GAAGCCTACG  CTCGCTGCCT  GAGGATGGGC    1080
TGTCGCTGCA  TCGAGTTGGA  CTGCTGGGAT  GGGCCAGATG  GGATGCCAGT  CATTTACCAT    1140
GGGCACACCC  TCACCACCAA  GATTAAGTTC  TCAGATGTCC  TGCACACCAT  CAAGGAGCAC    1200
GCGTTCGTAG  CCTCAGAGTA  CCCTGTCATC  CTGTCCATCG  AGGACCACTG  CAGCATTGCC    1260
CAGCAGAGGA  ACATGGCCCA  GCACTTCAGG  AAGGTGCTCG  GTGACACGCT  CCTCACCAAG    1320
```

-continued

```
CCCGTGGACA TTGCCGCTGA TGGGCTCCCT TCTCCCAACC AGCTCAAGAG GAAGATCCTG    1380
ATTAAGCATA AGAAGCTGGC TGAGGGCAGT GCCTATGAGG AGGTGCCTAC CTCTGTGATG    1440
TACTCTGAGA ATGACATCAG TAACTCCATC AAGAATGGTA TCCTCTACTT GGAGGACCCC    1500
GTGAATCATG AGTGGTACCC CCACTACTTT GTTCTGACTA GCAGCAAGAT CTACTACTCT    1560
GAGGAGACCA GCAGTGACCA GGGAAATGAG GATGAAGAGG AGCCGAAGGA GGCCAGTGGC    1620
AGCACAGAGC TGCACTCGAG CGAGAAGTGG TTCCACGGGA AGCTCGGGGC TGGGCGCGAC    1680
GGGCGGCACA TTGCTGAGCG CCTGCTCACC GAGTACTGCA TAGAGACTGG GGCTCCCGAT    1740
GGCTCCTTCC TAGTGCGAGA AAGTGAGACC TTCGTGGGGG ACTACACGCT GTCTTTTGG    1800
CGGAATGGGA AAGTCCAGCA CTGCCGTATC CACTCCCGGC AGGATGCTGG GACTCCTAAG    1860
TTCTTCTTGA CAGATAACCT TGTCTTTGAC TCTCTCTATG ACCTCATCAC ACATTATCAG    1920
CAAGTGCCCC TGCGCTGCAA TGAGTTTGAG ATGCGCCTTT CAGAGCCTGT TCCACAGACG    1980
AATGCCCATG AGAGCAAAGA GTGGTACCAC GCAAGCCTGA CTAGAGCTCA GGCTGAACAC    2040
ATGCTGATGC GAGTACCCCG TGATGGGGCC TTCCTGGTGC GGAAGCGCAA CGAGCCCAAC    2100
TCCTATGCCA TCTCTTTCCG GGCTGAGGGA AAGATCAAGC ACTGCCGAGT ACAGCAGGAA    2160
GGCCAGACTG TGATGCTGGG GAACTCTGAG TTTGACAGCC TGGTCGACCT CATCAGCTAC    2220
TATGAGAAGC ATCCCCTGTA CCGCAAAATG AAACTGCGCT ACCCCATCAA CGAGGAGGCG    2280
CTGGAGAAGA TTGGGACAGC TGAACCCGAT TATGGGGCAC TGTATGAGGG CCGCAACCCT    2340
GGTTTCTATG TGGAGGCCAA CCCTATGCCA ACTTTCAAGT GTGCAGTAAA AGCTCTCTTC    2400
GACTACAAGG CCCAGAGAGA GGATGAGCTG ACTTTTACCA AGAGCGCCAT CATCCAGAAT    2460
GTGGAAAAGC AAGATGGTGG CTGGTGGCGT GGGGACTATG GTGGGAAGAA GCAGCTGTGG    2520
TTCCCCTCAA ACTATGTGGA AGAGATGATC AATCCAGCAA TCCTAGAGCC GGAGAGGGAG    2580
CATCTGGATG AGAACAGCCC ACTGGGGGAC TTGCTGCGAG GGTCTTAGA TGTGCCAGCC    2640
TGCCAGATCG CCATTCGTCC TGAGGGCAAA AACAACCGGC TCTTCGTCTT CTCCATCAGC    2700
ATGCCGTCAG TGGCTCAGTG GTCCCTAGAC GTTGCCGCTG ACTCACAGGA GGAGTTGCAG    2760
GACTGGGTGA AAAAGATCCG TGAAGTTGCC CAGACTGCAG ATGCCAGGCT TACTGAGGGG    2820
AAGATGATGG AGCGGCGGAA GAAGATCGCC TTGGAGCTCT CCGAGCTCGT GGTCTACTGC    2880
CGGCCTGTTC CCTTTGACGA AGAGAAGATT GGCACAGAAC GCGCTTGTTA CCGGGACATG    2940
TCCTCCTTTC CGGAAACCAA GGCTGAGAAG TATGTGAACA AGGCCAAAGG CAAGAAGTTC    3000
CTCCAGTACA ACCGGCTGCA GCTCTCTCGC ATCTACCCTA AGGGTCAGAG GCTGGACTCC    3060
TCCAATTATG ACCCTCTGCC CATGTGGATC TGTGGCAGCC AGCTTGTAGC TCTCAATTTT    3120
CAGACCCCAG ACAAGCCTAT GCAGATGAAC CAGGCCCTCT TCATGGCTGG TGGACACTGT    3180
GGCTATGTGC TGCAGCCAAG CACCATGAGA GATGAAGCCT TTGACCCCTT TGATAAGAGC    3240
AGTCTCCGAG GTCTGGAGCC CTGTGTCATT TGCATTGAGG TGCTGGGGGC CAGGCATCTG    3300
CCGAAGAATG GCCGGGGTAT TGTGTGTCCT TTCGTGGAGA TTGAAGTGGC TGGGGCAGAG    3360
TACGACAGCA CCAAGCAGAA GACAGAGTTT GTAGTGGACA ATGGACTGAA CCCTGTGTGG    3420
CCTGCAAAGC CCTTCCACTT CCAGATCAGT AACCCAGAGT TTGCCTTTCT GCGCTTTGTG    3480
GTGTATGAGG AAGACATGTT TAGTGACCAG AACTTCTTGG CTCAGGCTAC TTTCCCAGTA    3540
AAAGGCCTGA AGACAGGATA CAGAGCAGTG CCTTTGAAGA ACAACTACAG TGAAGACCTG    3600
GAGTTGGCCT CCCTGCTCAT CAAGATTGAC ATTTTCCCTG CTAAGGAGAA TGGTGACCTC    3660
```

-continued

```
AGCCCTTTCA GTGGTACATC CCTAAGGGAA CGGGCCTCAG ATGCCTCCAG CCAGCTGTTC    3720

CATGTCCGGG CCCGGGAAGG GTCCTTTGAA GCCAGATACC AGCAGCCATT TGAAGACTTC    3780

CGCATCTCGC AGGAGCATCT CGCAGACCAT TTTGACAGTC GGGAACGAAG GGCCCCAAGA    3840

AGGACTCGGG TCAATGGAGA CAACCGCCTC                                     3870
```

( 2 ) INFORMATION FOR SEQ ID NO:2:

( i ) SEQUENCE CHARACTERISTICS:
        ( A ) LENGTH: 1290 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met  Ala  Gly  Ala  Ala  Ser  Pro  Cys  Ala  Asn  Gly  Cys  Gly  Pro  Ser  Ala
 1              5                    10                       15

Pro  Ser  Glu  Ala  Glu  Val  Leu  His  Leu  Cys  Arg  Ser  Leu  Glu  Val  Gly
              20                  25                       30

Thr  Val  Met  Thr  Leu  Phe  Tyr  Ser  Lys  Lys  Ser  Gln  Arg  Pro  Glu  Arg
              35                  40                       45

Lys  Thr  Phe  Gln  Val  Lys  Leu  Glu  Thr  Arg  Gln  Ile  Thr  Trp  Ser  Arg
       50                  55                       60

Gly  Ala  Asp  Lys  Ile  Glu  Gly  Ser  Ile  Asp  Ile  Arg  Glu  Ile  Lys  Glu
 65                  70                       75                       80

Ile  Arg  Pro  Gly  Lys  Thr  Ser  Arg  Asp  Phe  Asp  Arg  Tyr  Gln  Glu  Asp
                   85                  90                       95

Pro  Ala  Phe  Arg  Pro  Asp  Gln  Ser  His  Cys  Phe  Val  Ile  Leu  Tyr  Gly
                  100                 105                      110

Met  Glu  Phe  Arg  Leu  Lys  Thr  Leu  Ser  Leu  Gln  Ala  Thr  Ser  Glu  Asp
                  115                 120                      125

Glu  Val  Asn  Met  Trp  Ile  Lys  Gly  Leu  Thr  Trp  Leu  Met  Glu  Asp  Thr
            130                 135                      140

Leu  Gln  Ala  Ala  Thr  Pro  Leu  Gln  Ile  Glu  Arg  Trp  Leu  Arg  Lys  Gln
145                 150                      155                     160

Phe  Tyr  Ser  Val  Asp  Arg  Asn  Arg  Glu  Asp  Arg  Ile  Ser  Ala  Lys  Asp
                  165                      170                     175

Leu  Lys  Asn  Met  Leu  Ser  Gln  Val  Asn  Tyr  Arg  Val  Pro  Asn  Met  Arg
            180                      185                     190

Phe  Leu  Arg  Glu  Arg  Leu  Thr  Asp  Phe  Glu  Gln  Arg  Ser  Gly  Asp  Ile
            195                      200                 205

Thr  Tyr  Gly  Gln  Phe  Ala  Gln  Leu  Tyr  Arg  Ser  Leu  Met  Tyr  Ser  Ala
       210                      215                 220

Gln  Lys  Thr  Met  Asp  Leu  Pro  Phe  Leu  Glu  Thr  Asn  Thr  Leu  Arg  Thr
225                      230                 235                     240

Gly  Glu  Arg  Pro  Glu  Leu  Cys  Gln  Val  Ser  Leu  Ser  Glu  Phe  Gln  Gln
                  245                 250                      255

Phe  Leu  Leu  Glu  Tyr  Gln  Gly  Glu  Leu  Trp  Ala  Val  Asp  Arg  Leu  Gln
            260                 265                      270

Val  Gln  Glu  Phe  Met  Leu  Ser  Phe  Leu  Arg  Asp  Pro  Leu  Arg  Glu  Ile
            275                 280                      285

Glu  Glu  Pro  Tyr  Phe  Phe  Leu  Asp  Glu  Leu  Val  Thr  Phe  Leu  Phe  Ser
       290                 295                      300

Lys  Glu  Asn  Ser  Val  Trp  Asn  Ser  Gln  Leu  Asp  Ala  Val  Cys  Pro  Glu
```

-continued

```
        305                      310                      315                      320
Thr  Met  Asn  Asn  Pro  Leu  Ser  His  Tyr  Trp  Ile  Ser  Ser  Ser  His  Asn
                    325                      330                      335
Thr  Tyr  Leu  Thr  Gly  Asp  Gln  Phe  Ser  Ser  Glu  Ser  Ser  Leu  Glu  Ala
                    340                      345                      350
Tyr  Ala  Arg  Cys  Leu  Arg  Met  Gly  Cys  Arg  Cys  Ile  Glu  Leu  Asp  Cys
               355                      360                      365
Trp  Asp  Gly  Pro  Asp  Gly  Met  Pro  Val  Ile  Tyr  His  Gly  His  Thr  Leu
     370                      375                      380
Thr  Thr  Lys  Ile  Lys  Phe  Ser  Asp  Val  Leu  His  Thr  Ile  Lys  Glu  His
385                      390                      395                      400
Ala  Phe  Val  Ala  Ser  Glu  Tyr  Pro  Val  Ile  Leu  Ser  Ile  Glu  Asp  His
                    405                      410                      415
Cys  Ser  Ile  Ala  Gln  Gln  Arg  Asn  Met  Ala  Gln  His  Phe  Arg  Lys  Val
                    420                      425                      430
Leu  Gly  Asp  Thr  Leu  Leu  Thr  Lys  Pro  Val  Asp  Ile  Ala  Ala  Asp  Gly
               435                      440                      445
Leu  Pro  Ser  Pro  Asn  Gln  Leu  Lys  Arg  Lys  Ile  Leu  Ile  Lys  His  Lys
     450                      455                      460
Lys  Leu  Ala  Glu  Gly  Ser  Ala  Tyr  Glu  Glu  Val  Pro  Thr  Ser  Val  Met
465                      470                      475                      480
Tyr  Ser  Glu  Asn  Asp  Ile  Ser  Asn  Ser  Ile  Lys  Asn  Gly  Ile  Leu  Tyr
                    485                      490                      495
Leu  Glu  Asp  Pro  Val  Asn  His  Glu  Trp  Tyr  Pro  His  Tyr  Phe  Val  Leu
               500                      505                      510
Thr  Ser  Ser  Lys  Ile  Tyr  Tyr  Ser  Glu  Glu  Thr  Ser  Ser  Asp  Gln  Gly
               515                      520                      525
Asn  Glu  Asp  Glu  Glu  Glu  Pro  Lys  Glu  Ala  Ser  Gly  Ser  Thr  Glu  Leu
     530                      535                      540
His  Ser  Ser  Glu  Lys  Trp  Phe  His  Gly  Lys  Leu  Gly  Ala  Gly  Arg  Asp
545                      550                      555                      560
Gly  Arg  His  Ile  Ala  Glu  Arg  Leu  Leu  Thr  Glu  Tyr  Cys  Ile  Glu  Thr
                    565                      570                      575
Gly  Ala  Pro  Asp  Gly  Ser  Phe  Leu  Val  Arg  Glu  Ser  Glu  Thr  Phe  Val
               580                      585                      590
Gly  Asp  Tyr  Thr  Leu  Ser  Phe  Trp  Arg  Asn  Gly  Lys  Val  Gln  His  Cys
          595                      600                      605
Arg  Ile  His  Ser  Arg  Gln  Asp  Ala  Gly  Thr  Pro  Lys  Phe  Phe  Leu  Thr
     610                      615                      620
Asp  Asn  Leu  Val  Phe  Asp  Ser  Leu  Tyr  Asp  Leu  Ile  Thr  His  Tyr  Gln
625                      630                      635                      640
Gln  Val  Pro  Leu  Arg  Cys  Asn  Glu  Phe  Glu  Met  Arg  Leu  Ser  Glu  Pro
                    645                      650                      655
Val  Pro  Gln  Thr  Asn  Ala  His  Glu  Ser  Lys  Glu  Trp  Tyr  His  Ala  Ser
               660                      665                      670
Leu  Thr  Arg  Ala  Gln  Ala  Glu  His  Met  Leu  Met  Arg  Val  Pro  Arg  Asp
          675                      680                      685
Gly  Ala  Phe  Leu  Val  Arg  Lys  Arg  Asn  Glu  Pro  Asn  Ser  Tyr  Ala  Ile
     690                      695                      700
Ser  Phe  Arg  Ala  Glu  Gly  Lys  Ile  Lys  His  Cys  Arg  Val  Gln  Gln  Glu
705                      710                      715                      720
Gly  Gln  Thr  Val  Met  Leu  Gly  Asn  Ser  Glu  Phe  Asp  Ser  Leu  Val  Asp
                    725                      730                      735
```

-continued

| | | | | | | | | | | | | | | |
|---|---|---|---|---|---|---|---|---|---|---|---|---|---|---|
|Leu|Ile|Ser|Tyr 740|Tyr|Glu|Lys|His|Pro 745|Leu|Tyr|Arg|Lys|Met 750|Lys|Leu|
|Arg|Tyr|Pro 755|Ile|Asn|Glu|Glu|Ala 760|Leu|Glu|Lys|Ile|Gly 765|Thr|Ala|Glu|
|Pro|Asp 770|Tyr|Gly|Ala|Leu|Tyr 775|Glu|Gly|Arg|Asn|Pro 780|Gly|Phe|Tyr|Val|
|Glu 785|Ala|Asn|Pro|Met 790|Pro|Thr|Phe|Lys|Cys 795|Ala|Val|Lys|Ala|Leu|Phe 800|
|Asp|Tyr|Lys|Ala|Gln 805|Arg|Glu|Asp|Glu|Leu 810|Thr|Phe|Thr|Lys|Ser 815|Ala|
|Ile|Ile|Gln|Asn 820|Val|Glu|Lys|Gln|Asp 825|Gly|Gly|Trp|Trp|Arg 830|Gly|Asp|
|Tyr|Gly|Gly 835|Lys|Lys|Gln|Leu|Trp 840|Phe|Pro|Ser|Asn|Tyr 845|Val|Glu|Glu|
|Met|Ile 850|Asn|Pro|Ala|Ile|Leu 855|Glu|Pro|Glu|Arg|Glu 860|His|Leu|Asp|Glu|
|Asn 865|Ser|Pro|Leu|Gly|Asp 870|Leu|Leu|Arg|Gly|Val 875|Leu|Asp|Val|Pro|Ala 880|
|Cys|Gln|Ile|Ala|Ile 885|Arg|Pro|Glu|Gly|Lys 890|Asn|Asn|Arg|Leu|Phe 895|Val|
|Phe|Ser|Ile|Ser 900|Met|Pro|Ser|Val|Ala 905|Gln|Trp|Ser|Leu|Asp 910|Val|Ala|
|Ala|Asp|Ser 915|Gln|Glu|Glu|Leu|Gln 920|Asp|Trp|Val|Lys|Lys 925|Ile|Arg|Glu|
|Val|Ala|Gln 930|Thr|Ala|Asp|Ala|Arg 935|Leu|Thr|Glu|Gly|Lys 940|Met|Met|Glu|
|Arg 945|Arg|Lys|Lys|Ile|Ala 950|Leu|Glu|Leu|Ser|Glu 955|Leu|Val|Val|Tyr|Cys 960|
|Arg|Pro|Val|Pro|Phe 965|Asp|Glu|Glu|Lys|Ile 970|Gly|Thr|Glu|Arg|Ala 975|Cys|
|Tyr|Arg|Asp|Met 980|Ser|Ser|Phe|Pro|Glu 985|Thr|Lys|Ala|Glu|Lys 990|Tyr|Val|
|Asn|Lys|Ala|Lys 995|Gly|Lys|Lys|Phe|Leu 1000|Gln|Tyr|Asn|Arg|Leu 1005|Gln|Leu|
|Ser|Arg|Ile|Tyr 1010|Pro|Lys|Gly|Gln|Arg 1015|Leu|Asp|Ser|Ser|Asn 1020|Tyr|Asp|
|Pro 1025|Leu|Pro|Met|Trp|Ile 1030|Cys|Gly|Ser|Gln|Leu 1035|Val|Ala|Leu|Asn|Phe 1040|
|Gln|Thr|Pro|Asp|Lys 1045|Pro|Met|Gln|Met|Asn 1050|Gln|Ala|Leu|Phe|Met 1055|Ala|
|Gly|Gly|His|Cys 1060|Gly|Tyr|Val|Leu|Gln 1065|Pro|Ser|Thr|Met|Arg 1070|Asp|Glu|
|Ala|Phe|Asp 1075|Pro|Phe|Asp|Lys|Ser 1080|Ser|Leu|Arg|Gly|Leu 1085|Glu|Pro|Cys|
|Val|Ile|Cys 1090|Ile|Glu|Val|Leu|Gly 1095|Ala|Arg|His|Leu|Pro 1100|Lys|Asn|Gly|
|Arg 1105|Gly|Ile|Val|Cys|Pro 1110|Phe|Val|Glu|Ile|Glu 1115|Val|Ala|Gly|Ala|Glu 1120|
|Tyr|Asp|Ser|Thr|Lys 1125|Gln|Lys|Thr|Glu|Phe 1130|Val|Val|Asp|Asn|Gly 1135|Leu|
|Asn|Pro|Val|Trp 1140|Pro|Ala|Lys|Pro|Phe 1145|His|Phe|Gln|Ile|Ser 1150|Asn|Pro|

|  |  |  |  |  |  |  |  |  |  |  |  |  |  |
|---|---|---|---|---|---|---|---|---|---|---|---|---|---|
| Glu | Phe | Ala<br>1155 | Phe | Leu | Arg | Phe | Val<br>1160 | Val | Tyr | Glu | Glu<br>1165 | Asp | Met | Phe | Ser |

Asp Gln Asn Phe Leu Ala Gln Ala Thr Phe Pro Val Lys Gly Leu Lys
        1170            1175             1180

Thr Gly Tyr Arg Ala Val Pro Leu Lys Asn Asn Tyr Ser Glu Asp Leu
1185             1190              1195                    1200

Glu Leu Ala Ser Leu Leu Ile Lys Ile Asp Ile Phe Pro Ala Lys Glu
              1205            1210                  1215

Asn Gly Asp Leu Ser Pro Phe Ser Gly Thr Ser Leu Arg Glu Arg Ala
                1220          1225            1230

Ser Asp Ala Ser Ser Gln Leu Phe His Val Arg Ala Arg Glu Gly Ser
            1235              1240            1245

Phe Glu Ala Arg Tyr Gln Gln Pro Phe Glu Asp Phe Arg Ile Ser Gln
    1250              1255          1260

Glu His Leu Ala Asp His Phe Asp Ser Arg Glu Arg Arg Ala Pro Arg
1265              1270            1275                  1280

Arg Thr Arg Val Asn Gly Asp Asn Arg Leu
            1285              1290

(2) INFORMATION FOR SEQ ID NO:3:

( i ) SEQUENCE CHARACTERISTICS:
        ( A ) LENGTH: 3893 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
ATGGCGGGCG  CCGCGTCCCC  CTGCGCCAAC  GGCTGCGGGC  CCAGCGCGCC  CTCCGAAGCG    60
GAGGTGCTGC  ACCTCTGCCG  CAGCCTCGAG  GTGGGCACCG  TCATGACTTT  GTTCTACTCC   120
AAGAAGTCGC  AGCGGCCAGA  ACGGAAGACC  TTCCAGGTCA  AGTTGGAGAC  GCGCCAGATC   180
ACATGGAGCC  GCGGTGCGGA  CAAAATCGAG  GGGTCCATCG  ATATCCGAGA  AATCAAGGAG   240
ATCCGCCCAG  GGAAGACTTC  CCGGGACTTT  GACCGCTACC  AAGAAGACCC  TGCCTTCCGG   300
CCAGATCAGT  CACACTGTTT  TGTCATCCTC  TATGGAATGG  AATTCCGCCT  GAAGACCCTG   360
AGCCTGCAAG  CCACATCTGA  GGATGAAGTG  AACATGTGGA  TCAAGGGCTT  AACTTGGCTC   420
ATGGAAGATA  CGCTGCAGGC  GGCCACACCC  TGCAAATTG   AGAGATGGCT  CCGGAAGCAG   480
TTCTACTCAG  TGGATCGTAA  CCGAGAGGAT  CGTATATCAG  CCAAGGACCT  GAAGAACATG   540
CTGTCACAGG  TCAACTACCG  GGTCCCCAAC  ATGCGCTTCC  TCCGAGAGCG  GCTGACGGAC   600
TTTGAACAGC  GCAGCGGGGA  CATCACCTAT  GGGCAGTTTG  CTCAGCTTTA  CCGCAGCCTC   660
ATGTACAGCG  CCCAGAAGAC  GATGGACCTT  CCGTTCTTGG  AAACCAACAC  TTTGAGGACT   720
GGAGAGCGGC  CAGAGCTTTG  CCAGGTGTCC  CTTTCTGAGT  TCCAGCAGTT  CCTTCTTGAG   780
TACCAGGGGG  AGCTGTGGGC  TGTCGACCGG  CTTCAGGTGC  AGGAATTTAT  GCTCAGCTTC   840
CTTCGAGACC  CCTTGCGAGA  GATTGAGGAG  CCATACTTCT  TCTTGGATGA  GCTTGTCACC   900
TTTCTGTTCT  CCAAAGAGAA  CAGTGTGTGG  AACTCACAGC  TGGATGCCGT  GTGCCCAGAA   960
ACCATGAACA  ACCCACTGTC  TCACTATTGG  ATCTCTTCCT  CGCATAATAC  GTATCTGACT  1020
GGGGACCAGT  TCTCCAGCGA  GTCCTCCCTG  GAAGCCTACG  CTCGCTGCCT  GAGGATGGGC  1080
TGTCGCTGCA  TCGAGTTGGA  CTGCTGGGAT  GGGCCAGATG  GGATGCCAGT  CATTTACCAT  1140
GGGCACACCC  TCACCACCAA  GATTAAGTTC  TCAGATGTCC  TGCACACCAT  CAAGGAGCAC  1200
```

| | | | | | | |
|---|---|---|---|---|---|---|
| GCGTTCGTAG | CCTCAGAGTA | CCCTGTCATC | CTGTCCATCG | AGGACCACTG | CAGCATTGCC | 1260 |
| CAGCAGAGGA | ACATGGCCCA | GCACTTCAGG | AAGGTGCTCG | GTGACACGCT | CCTCACCAAG | 1320 |
| CCCGTGGACA | TTGCCGCTGA | TGGGCTCCCT | TCTCCCAACC | AGCTCAAGAG | GAAGATCCTG | 1380 |
| ATTAAGCATA | AGAAGCTGGC | TGAGGGCAGT | GCCTATGAGG | AGGTGCCTAC | CTCTGTGATG | 1440 |
| TACTCTGAGA | ATGACATCAG | TAACTCCATC | AAGAATGGTA | TCCTCTACTT | GGAGGACCCC | 1500 |
| GTGAATCATG | AGTGGTACCC | CCACTACTTT | GTTCTGACTA | GCAGCAAGAT | CTACTACTCT | 1560 |
| GAGGAGACCA | GCAGTGACCA | GGGAAATGAG | GATGAAGAGG | AGCCGAAGGA | GGCCAGTGGC | 1620 |
| AGCACAGAGC | TGCACTCGAG | CGAGAAGTGG | TTCCACGGGA | AGCTCGGGGC | TGGGCGCGAC | 1680 |
| GGGCGGCACA | TTGCTGAGCG | CCTGCTCACC | GAGTACTGCA | TAGAGACTGG | GGCTCCCGAT | 1740 |
| GGCTCCTTCC | TAGTGCGAGA | AAGTGAGACC | TTCGTGGGGG | ACTACGCT | GTCTTTTGG | 1800 |
| CGGAATGGGA | AAGTCCAGCA | CTGCCGTATC | CACTCCCGGC | AGGATGCTGG | GACTCCTAAG | 1860 |
| TTCTTCTTGA | CAGATAACCT | TGTCTTTGAC | TCTCTCTATG | ACCTCATCAC | ACATTATCAG | 1920 |
| CAAGTGCCCC | TGCGCTGCAA | TGAGTTTGAG | ATGCGCCTTT | CAGAGCCTGT | TCCACAGACG | 1980 |
| AATGCCCATG | AGAGCAAAGA | GTGGTACCAC | GCAAGCCTGA | CTAGAGCTCA | GGCTGAACAC | 2040 |
| ATGCTGATGC | GAGTACCCCG | TGATGGGGCC | TTCCTGGTGC | GGAAGCGCAA | CGAGCCCAAC | 2100 |
| TCCTATGCCA | TCTCTTTCCG | GGCTGAGGGA | AAGATCAAGC | ACTGCCGAGT | ACAGCAGGAA | 2160 |
| GGCCAGACTG | TGATGCTGGG | GAACTCTGAG | TTTGACAGCC | TGGTCGACCT | CATCAGCTAC | 2220 |
| TATGAGAAGC | ATCCCCTGTA | CCGCAAAATG | AAACTGCGCT | ACCCCATCAA | CGAGGAGGCG | 2280 |
| CTGGAGAAGA | TTGGGACAGC | TGAACCCGAT | TATGGGGCAC | TGTATGAGGG | CCGCAACCCT | 2340 |
| GGTTTCTATG | TGGAGGCCAA | CCCTATGCCA | ACTTTCAAGT | GTGCAGTAAA | AGCTCTCTTC | 2400 |
| GACTACAAGG | CCCAGAGAGA | GGATGAGCTG | ACTTTTACCA | AGAGCGCCAT | CATCCAGAAT | 2460 |
| GTGGAAAAGC | AAGATGGTGG | CTGGTGGCGT | GGGGACTATG | GTGGGAAGAA | GCAGCTGTGG | 2520 |
| TTCCCCTCAA | ACTATGTGGA | AGAGATGATC | AATCCAGCAA | TCCTAGAGCC | GGAGAGGGAG | 2580 |
| CATCTGGATG | AGAACAGCCC | ACTGGGGGAC | TTGCTGCGAG | GGGTCTTAGA | TGTGCCAGCC | 2640 |
| TGCCAGATCG | CCATTCGTCC | TGAGGGCAAA | AACAACCGGC | TCTTCGTCTT | CTCCATCAGC | 2700 |
| ATGCCGTCAG | TGGCTCAGTG | GTCCCTAGAC | GTTGCCGCTG | ACTCACAGGA | GGAGTTGCAG | 2760 |
| GACTGGGTGA | AAAAGATCCG | TGAAGTTGCC | CAGACTGCAG | ATGCCAGGCT | TACTGAGGGG | 2820 |
| AAGATGATGG | AGCGGCGGAA | GAAGATCGCC | TTGGAGCTCT | CCGAGCTCGT | GGTCTACTGC | 2880 |
| CGGCCTGTTC | CCTTTGACGA | AGAGAAGATT | GGCACAGAAC | GCGCTTGTTA | CCGGGACATG | 2940 |
| TCCTCCTTTC | CGGAAACCAA | GGCTGAGAAG | TATGTGAACA | AGGCCAAAGG | CAAGAAGTTC | 3000 |
| CTCCAGTACA | ACCGGCTGCA | GCTCTCTCGC | ATCTACCCTA | AGGGTCAGAG | GCTGGACTCC | 3060 |
| TCCAATTATG | ACCCTCTGCC | CATGTGGATC | TGTGGCAGCC | AGCTTGTAGC | TCTCAATTTT | 3120 |
| CAGACCCCAG | ACAAGCCTAT | GCAGATGAAC | CAGGCCCTCT | TCATGGCTGG | TGGACACTGT | 3180 |
| GGCTATGTGC | TGCAGCCAAG | CACCATGAGA | GATGAAGCCT | TGACCCCTT | TGATAAGAGC | 3240 |
| AGTCTCCGAG | GTCTGGAGCC | CTGTGTCATT | TGCATTGAGG | TGCTGGGGGC | CAGGCATCTG | 3300 |
| CCGAAGAATG | GCCGGGGTAT | TGTGTGTCCT | TTCGTGGAGA | TTGAAGTGGC | TGGGGCAGAG | 3360 |
| TACGACAGCA | CCAAGCAGAA | GACAGAGTTT | GTAGTGGACA | ATGGACTGAA | CCCTGTGTGG | 3420 |
| CCTGCAAAGC | CCTTCCACTT | CCAGATCAGT | AACCCAGAGT | TTGCCTTTCT | GCGCTTTGTG | 3480 |
| GTGTATGAGG | AAGACATGTT | TAGTGACCAG | AACTTCTTGG | CTCAGGCTAC | TTTCCCAGTA | 3540 |

| | | | | | | |
|---|---|---|---|---|---|---|
| AAAGGCCTGA | AGACAGGATA | CAGAGCAGTG | CCTTTGAAGA | ACAACTACAG | TGAAGACCTG | 3600 |
| GAGTTGGCCT | CCCTGCTCAT | CAAGATTGAC | ATTTTCCCTG | CTAAGGAGAA | TGGTGACCTC | 3660 |
| AGCCCTTTCA | GTGGTACATC | CCTAAGGGAA | CGGGCCTCAG | ATGCCTCCAG | CCAGCTGTTC | 3720 |
| CATGTCCGGG | CCCGGGAAGG | GTCCTTTGAA | GCCAGATACC | AGCAGCCATT | TGAAGACTTC | 3780 |
| CGCATCTCGC | AGGAGCATCT | CGCAGACCAT | TTTGACAGTC | GGGAACGAAG | GGCCCCAAGA | 3840 |
| AGGACTCGGG | TCAATGGAGA | CAACCGCCTC | GAAGAATTTT | AGTCTAGAAG | CTT | 3893 |

(2) INFORMATION FOR SEQ ID NO:4:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

| | | | | | |
|---|---|---|---|---|---|
| CCCGGGCATA | TGGATCCATT | GGAGGATGAT | TAAATGGCGG | GCGCCGCGTC C | 51 |

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

| | | |
|---|---|---|
| CTGCTTCCGG | AGCCACCTCT C | 21 |

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

| | | |
|---|---|---|
| TCGCCATTCG | TCCTGAGGGC | 20 |

(2) INFORMATION FOR SEQ ID NO:7:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

| | | | | | |
|---|---|---|---|---|---|
| GGGCCCAAGC | TTCTAGACTA | AAATTCTTCG | AGGCGGTTGT | CTCCATTGAC | CCGAGTTCGT | 60 |
| CG | | | | | | 62 |

(2) INFORMATION FOR SEQ ID NO:8:

(i) SEQUENCE CHARACTERISTICS:
        (A) LENGTH: 26 base pairs ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

GATGATGGAG CGGCGGAAGA AGATCG 26

( 2 ) INFORMATION FOR SEQ ID NO:9:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

CGATCTTCTT CCGCCGCTCC ATCATC 26

EXPRESSION AND PURIFICATION OF PHOSPHOINOSITIDE-SPECIFIC PHOSPHOLIPASE C-γ

BACKGROUND OF THE INVENTION

Phospholipases C (EC 3.1.4.3) are a family of enzymes which hydrolyze the sn-3 phosphodiester bond in membrane phospholipids producing diacylglycerol and a phosphorylated polar head group. Mammalian phospholipase C (PLC) enzymes exhibit specificity for the polar head group which is hydrolyzed, i.e., phosphatidylcholine, phosphatidylinositol, etc. Recently, much interest has been generated in those PLC enzymes which selectively hydrolyze phosphoinositide lipids in response to receptor occupancy by agonist. Hydrolysis of phosphatidylinositol 4,5-bisphosphate generates two second messenger molecules; diacylglycerol, a co-factor required for activation of protein kinase C, and inositol 1,4,5-trisphosphate, a soluble second messenger molecule which promotes the release of intracellular non-mitochrondrial stores of calcium (Berridge, $Ann.$ $Rev.$ $Biochem.$, 56:159–193, 1987). The diacylglycerol released may be further metabolized to free arachidonic acid by sequential actions of diglycerol lipase and monoglycerol lipase. Thus, phospholipases C are not only important enzymes in the generation of second messenger molecules, but may serve an important role in making arachidonic acid available for eicosanoid biosynthesis in select tissues.

Mammalian tissues contain multiple distinct forms of phosphoinositide-specific PLC (Crooke and Bennett, $Cell$ $Calcium$, 10:309–323, 1989; Rhee et al., $Science$, 244:546–550, 1989). It is proposed that each of the enzymes couple to distinct classes of cell surface receptors, i.e., PLC-α couples to vasopressin receptors, PLC-γ couples to growth factor receptors, etc. (Aiyar et al., $Biochem.$ $J.$, 261:63–70, 1989; Crooke and Bennett, $Cell$ $Calcium$, 10:309–323, 1989; Margolis et al., $Cell$, 57:1101–1107, 1989; Wahl et al., $Proc.$ $Natl.$ $Acad.$ $Sci.$ $USA$, 86:1568–1572, 1989). PLCγ$_1$ contains src-homology regions (SH2 and SH3) that appear to mediate the interaction between the enzyme and receptors with tyrosine kinase activity, such as the epidermal growth factor (EGF) receptor (Stahl et al. $Nature$, 332:269–272 (1988); Katan et al., $Cell$, 54:171–177 (1988)).

It has been established that a rapid synthesis of prostaglandins (PG) from arachidonic acid in macrophages usually accompanies inflammatory stimuli. Thus, inhibition of the release of arachidonic acid from macrophages would provide an effective control of PG synthesis and thereby inflammatory conditions. Recently, phospholipase C has been characterized as an enzyme which is involved in the biosynthetic phosphatidylinositol-arachidonic acid-prostaglandin pathway. This finding is further substantiated by the observation that phospholipase C is inhibited by phenothiazine, a compound known to inhibit the stimulated release of arachidonic acid from macrophages and prostaglandins from platelets.

PLCγ is the only isozyme that is phosphorylated by activated tyrosine kinase growth factor receptors (Rotin et al., $EMBO$ $J.$, 11:559–567 (1992); Mohammadi et al., $Mol.$ $Cell.$ $Biol.$, 11:5068–5078 (1992); Kim et al., $Cell$, 65:435–441 (1991)). Following growth factor stimulation, cytosolic PLCγ is extensively and rapidly phosphorylated in vivo (50–70% of the PLCγ molecules are modified within 5 minutes). This phosphorylation apparently induces the relocation of PLCγ to the plasma membrane where presumably it is better able to interact with its phospholipid substrates. In vitro studies utilizing enzyme that had previously been immunoprecipitated from cells suggest that the catalytic activity of the phosphorylated form of PLCγ$_1$ is increased compared to that of the unphosphorylated form, although this effect also depends on the assay conditions. These results suggest that PLCγ may be an important component of mitogenic signal transduction. Furthermore, altered PLCγ activity may correlate with some disease states. For example, an increase in the concentration of PLCγ has been documented in cells derived from primary human breast carcinomas which also overexpress the EGF receptor (Arteaga et al., $Proc.$ $Natl.$ $Acad.$ $Sci.$ $U.S.A.$, 88, 10435–10439 (1991)). Thus, inhibition of PLCγ activity, particularly of the activated form, may be of therapeutic value in the treatment of breast cancer.

All mammalian tissues which have been studied exhibit one or more PI-PLC enzymes. Generally, more than one enzyme exists in a single mammalian cell type. PI-PLC enzymes do exhibit tissue selectivity in their distribution. PLC-γ is found predominantly in neural tissues and is the major enzyme in the brain. However, isolation of the enzyme from mammalian tissue involves cumbersome organic solvent extractions and only limited quantities of enzyme can be obtained in this way. No information is available concerning the genetic regulation of PI-PLC enzymes, mRNA or protein stability.

To date, the cDNA for 6 distinct PI-PLC enzymes have been cloned. The enzymes range in size from 504 amino acids to 1250 amino acids, and are remarkably divergent considering that they exhibit similar biochemical properties. Four of the five enzymes (PLC-β, PLC-δ1, PLC-δ2, and PLC-α) contain two domains approximately 250 amino acids in length which exhibit between 50 to 80% sequence similarity. PLC-α contains sequences with 35% similarity to the first domain only (Crooke and Bennett, $Cell$ $Calcium$, 10:309–323, 1989). The marked differences in DNA sequences for the different PI-PLC enzyme allows the selective targeting of one PI-PLC enzyme, without affecting other enzymes using antisense technology. The human cDNA clone has been reported for PLC-δ$_1$ and PLC-δ$_2$, (Ohta et al., $FEBS$ $Lett.$, 242:31–35, 1988) and PLC-γ1 (Burgess et al., $Mol.$ $Cell.$ $Biol.$, 10:4770–4777 (1990)). The rest are rat cDNA clones. The genomic clones have not been reported for any of the PI-PLC enzymes.

Expression and purification of phospholipase C-δ$_1$ as a fusion protein in $E.$ $coli$ has been previously reported (R. Ginger and P. Parker, $Eur.$ $J.$ $Biochem.$, 210:155–160(1992). The expression and purification of rat phospholipase C-δ$_1$ in $E.$ $coli$ has also been reported by M. Ellis et al. ($Eur.$ $J.$ $Biochem.$, 213:339–347(1993)), however the expression system utilized resulted in either largely insoluble protein or such a low expression that the specific activity of the full length enzyme could not be determined. There are reports of expression of rat phospholipase C-γ in $E.$ $coli$ where no purification of the enzyme was attempted (Y. Emori et al., $J.Biol.$ $Chem$ . . , 264:21885–21890 (1989)).

The cloning of bovine brain phospholipase Cγ has been previously reported (M. L. Stahl et al., $Nature$, 332:269–272 (1988)) and the enzyme has been expressed in mammalian cells. Proof of the expression in mammalian cells was only by PLC activity of the cell lysates and the enzyme was never isolated.

Accordingly, it is an object of this invention to provide a convenient process for the preparation of phospholipase Cγ which is isolated in an active soluble form.

It is also the object of this invention to provide a cDNA construct which can be used to express such a phospholipase Cγ.

Another object of this invention is to provide a convenient assay for phospholipase Cγ activity which can be used to identify inhibitors of such activity.

Figure 1:
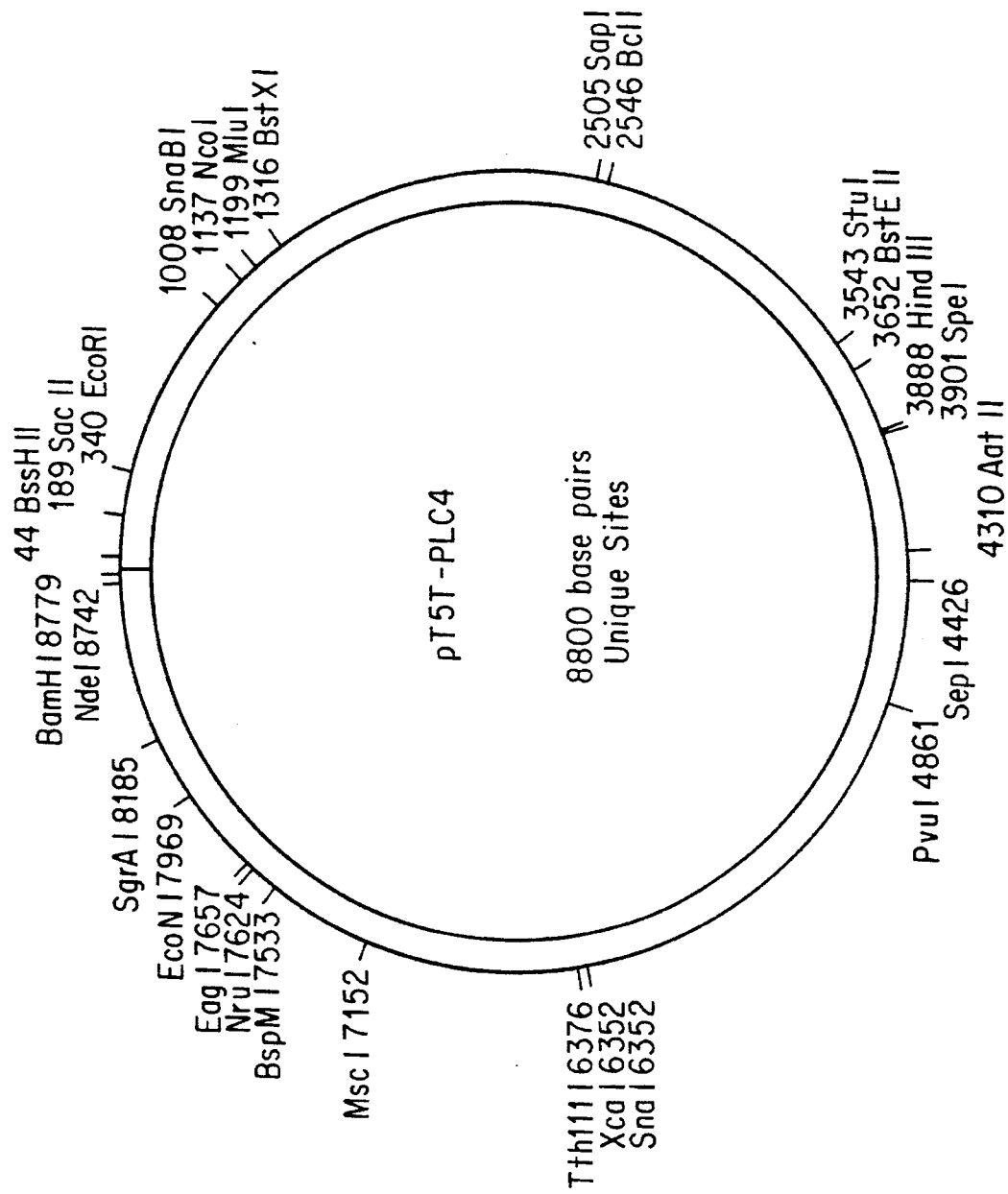
FIG. 1. Plasmid pT5T-PLC4

A schematic depiction of the construction of plasmid pT5T-PLC4 is shown.

FIG. 2. PLCγ$_1$ amino acid sequence and cDNA encoding sequence

The nucleotide sequence which encodes PLC γ$_1$ is shown along with the corresponding amino acids of PLC γ$_1$ which are provided underneath the cDNA sequence. The codons at 2833–2838 have been changed from the natural AGGAGG tandem to CGGCGG. (cDNA: SEQ.ID.NO.: 1; amino acid: SEQ.ID.NO.: 2)

FIG. 3. cDNA encoding sequence which includes the epitope tag

Nucleotide sequence used for expression and purification of PLC γ$_1$ (1– 3879; end indicated by "*") and the neighboring BamII restriction site. The amino acid sequence of the longest open reading frame (1291 aa) is provided underneath the corresponding nucleotides. (cDNA: SEQ.ID.NO.: 3; amino acid: SEQ.ID.NO.: 2)

DETAILED DESCRIPTION OF THE INVENTION

A host cell is transformed with a plasmid containing cDNA encoding phospholipase Cγ.

The host cell may be any cell capable of expressing the phospholipase Cγ. Such a cell line includes bacterial cells which may be selected from strains of *Escherichia coli*, such as DH5, HB 101, BL21 (DE3) and the like. The host cell may also be selected from yeast cells, such as *Saccharomyces cerevisiae* and the like, mammalian cells, such as human embryonic kidney 293 cells and the like, and insects cells, such as Sf9 cells where expression is mediated by bacculovirus and the like.

The cDNA encoding the phospholipase Cγ may be selected from cDNAs of any mammal, such as human, bovine or rat and the like, and from any variety of mammalian cells, tissues or organs. Preferably the cDNA selected codes for the PLCγ of rat brain cells The plasmid vector into which the eDNA encoding the mammalian phospholipase Cγ is cloned may be any vector compatible with transformation into the selected bacterial cell line. Such vectors include, but are not limited to, derivatives of ColE1 (such as pBR322, pUC8, pUC9, pUC18, pUC19, and the like) (Yanish-Perron et al, 1985, *Gene*,33:103–119) or P15a (such as pACYC177, pACYC184, and the like) (A. C. Y. C. Chang and S. N. Cohen, 1978, *J. Bacteriology*, 134:1141– 1156).

To ensure translation of the transcribed cDNA sequences, a ribosomal binding site must be operationally linked to the phospholipase CT coding sequences. An example of a ribosomal binding site GGAG encoded in the Glu-Glu-Phe epitope tag which can be placed at the C-terminal end of the coding sequence.

The transformed cell line is grown and harvested and the mammalian phospholipase Cγ expressed by the cells is isolated and purified. Isolation and purification of the mammalian phospholipase Cγ may be accomplished by any of the techniques well known to persons skilled in the art. For instance, after the cell extract is prepared the enzyme may be subjected to two partial purification steps prior to affinity chromatography. These steps comprise preliminary treatment with 30% saturated ammonium sulfate which removes certain contaminants by precipitation. This is followed by treatment with 50% saturated ammonium sulfate, which precipitates the PLCγ. The pelleted enzyme is then dissolved, preferably in a solution of 20 mM Tris-chloride (ph 7.5) containing 1 mM DTT and 20 gM $ZnCl_2$. After dialysis against the same buffer the enzyme solution is applied to an ion exchange column containing an ion exchange resin such as Mono Q. After washing of the column, the enzyme is eluted with a gradient of 0.25–1.0 M NaCl in the same buffer. The enzyme activity in each fraction is assayed as described below, and the fractions containing activity are pooled and applied to the affinity column described below.

It is, of course, recognized that the preliminary purification steps described above are preferred laboratory procedures that might readily be replaced with other procedures of equivalent effect such as ion exchange chromatography on other resins or gel filtration chromatography. Indeed, it is possible that these steps could even be omitted and the crude cell extract might be carried directly to affinity chromatography.

After the preliminary purification steps, the extract may be subjected to affinity chromatography on an affinity chromatography medium which includes a PLCγ binding peptide coupled to a suitable matrix.

The next step in the overall general purification scheme involves simply washing the medium to remove impurities. That is, after subjecting the extract to affinity chromatography on the affinity matrix, one will desire to wash the matrix in a manner that will remove the impurities while leaving the PLCγ relatively intact on the medium. A variety of techniques are known in the art for washing matrices such as the one employed herein, and all such washing techniques are intended to be included within the scope of this invention. Of course, for washing purposes, one will not desire to employ buffers that will release or otherwise alter or denature the enzyme. Thus, one will typically want to employ buffers which contain non-denaturing detergents such as octylglucoside buffers.

After the matrix-bound enzyme has been sufficiently washed, for example in a medium-ionic strength buffer at essentially neutral pH, the specifically bound material can be eluted from the column by using a similar buffer but of reduced pH (for example, a pH of between about 4 and 5.5). At this pH, the enzyme will typically be found to elute from the preferred affinity matrices disclosed in more detail hereinbelow. Typically the enzyme is eluted into a neutralizing buffer to prevent deleterious effects of the buffer having reduced pH.

While it is believed that advantages in accordance with the invention can be realized simply through affinity chromatography techniques, additional benefits will be achieved through the application of additional purification techniques, such as gel filtration techniques. For example, the inventors have discovered that Sephacryl S-200 high resolution gel columns can be employed with significant benefit in terms of enzyme purification. However, the present disclosure is by no means limited to the use of Sephacryl S-200, and it is believed that virtually any type of gel filtration arrangement can be employed with some degree of benefit. For example, one may wish to use techniques such as gel filtration, employing media such as Superose, Agarose, or even Sephadex.

Preferably an epitope tag is incorporated in the PLCγ when it is expressed and the cell lysate is exposed to a column containing an antibody which binds to the tagging amino acid sequence. Most preferably the phospholipase Cγ is tagged with a C-terminal EEF epitope and the column utilized is a column containing monoclonal antibody YL1/2 (described in J. V. Kilmartin et al., *J. Cell Biology*, 93: 576–582(1982)).

The recombinantly expressed, mammalian phospholipase Cγ is employed in an assay to determine the inhibitory activity against phospholipase Cγ of various pharmaceutical compounds. The assay is accomplished by reacting phosphatidylinositol or partially hydrolyzed phosphatidylinositol such as phosphatidylinositol 4,5-bisphosphate and the like, in a buffer solution, such as a solution containing Na-HEPES, sodium deoxycholate and a calcium cation source and similar buffer solutions, in the presence of the PLCγ enzyme. When the inhibitory activity of a pharmaceutical compound is to be determined the pharmaceutical compound that is to be tested is mixed with the buffer/phosphatidylinositol solution prior to the addition of the enzyme.

It is understood that the recombinantly prepared enzyme may be employed in either a purified or unpurified state. Thus, the crude bacterial cell extracts may be employed in the assay provided sufficient PLCγ activity can be determined to allow for comparison of activity in the presence of a test compound. Preferably, the PLCγ$_1$ is at least partially purified, for instance through the use of affinity chromatography. Most preferably the enzyme is in a highly purified state after exposed to the sequential purification step described hereinabove and in the examples.

The calcium cation source the is employed in the assay may be any source of Ca$^{++}$ such as calcium chloride, calcium iodide and the like.

Determination of the extent to which the phosphatidylinositol or hydrolyzed phosphatidylinositol is further hydrolyzed may be determined by analytical chromatographic techniques well known in the art. Alternatively, radioactively labeled phosphatidylinositol, such as [$^3$H]-phosphatidylinositol and the like, may be employed and the extent of hydrolysis may be determined by the use of a scintillation counter.

The reaction conditions used in the PLCγ assay may be adjusted to optimize the hydrolysis in vitro. For example, using reaction conditions described in the example herein, appropriate concentrations of cations such as Mg$^{++}$, Mn$^{++}$ or Cd$^{++}$ may be added to the assay buffer, as long as sufficient concentration of Ca$^{++}$ is present. Likewise, agents such as DTT, which protect sulfhydryl groups, may be added to the assay mixture. Although PLCγ is active at a wide range of pHs, optimal activity may be achieved by adjusting the pH between 6.8 and 8.0.

The invention is further defined by reference to the following example, which is illustrative and not limiting. All temperatures are in degrees Celsius.

EXAMPLE

Assay Protocol for Evaluating Inhibition of Phospholipase Cγ$_1$

General. Competent DH5α cells (subcloning efficiency) were obtained from GIBCO/BRL (Gaithersburg, Md.). Competent BL21(DE3) cells were purchased from Novagen (Madison, Wis.). PCR mutagenesis was carried out according to literature protocol (Higuchi, (1990). The general cloning vector, pBSII(S/K)+, was from Stratagene (La Jolla, Calif.). pT5T was constructed as described (Eisenberg et al., 1990). DNA sequencing was performed at each sequence modification on the relevant portion of the gene using the dideoxy chain termination method (Sanger et al., 1977) to verify the change to the wild type cDNA. Standard DNA manipulations were carried out as described (Sambrook et al., 1989 ).

Oligonucleotides. Synthetic deoxyribonucleotides were obtained from Midland Certified Reagent Co. (Midland, Tex.). The sequences of the oligonucleotides are (5' to 3'):

---

01 CCC—GGG—CAT—ATG—GAT—CCA—TTG—GAG—GAT—GAT—TAA—ATG—GCG—GGC—GCC—GCG—TCC (SEQ. ID. NO.: 4)

02 CTG—CTT—CCG—GAG—CCA—CCT—CTC (SEQ. ID. NO.: 5)

03 TC—GCC—ATT—CGT—CCT—GAG—GGC (SEQ. ID. NO.: 6)

04 GG—GCC—CAA—GCT—TCT—AGA—CTA—AAA—TTC—TTC—GAG—GCG—GTT—GTC—TCC—ATT—GAC—CCG—AGT—TCG—TCG (SEQ. ID. NO.: 7)

05 G—ATG—ATG—GAG—CGG—CGG—AAG—AAG—ATC—G (SEQ. ID. NO.: 8)

06 C—GAT—CTT—CTT—CCG—CCG—CTC—CAT—CAT—C (SEQ. ID. NO.: 9)

---

Subcloning of the PLCγ$_1$ Coding Sequence. Rat brain cDNA is synthesized using rat brain poly(A)RNA as template by literature protocol (Sambrook, J. et al., *Molecular Cloning: A Laboratory Manual*, Cold Spring Harbor Laboratory Press, Cold Spring Harbor, N.Y.). From the published cDNA sequence of rat brain PLCγ$_1$ (Suh, P. -G., Ryu, S. H., Moon, K. H., Suh, H. W., & Rhee, S. G. (1988) *Proc. Natl. Acad. Sci. USA* 85, 5419–5423), PCR primers, one which contains a BamHI restriction site upstream of the sequence complementary to the 5' end of the PLCγ gene (primer 01 ), and the other one which contains a HindIII site downstream of the 3' end of the PLCγ gene (primer 04), were synthesized. Carrying out the PCR using these primers (01 and 04) with the above mentioned rat brain cDNA as template, a DNA fragment with the entire rat brain PLCγ$_1$ coding sequence, flanked by a 5' BamHI site and a 3' HindIII site, is generated. This BamHI-HindIII fragment containing the coding sequence of PLCγ$_1$ was subcloned into pBSII(S/K)+, generating pPLC1. The rest of the manipulations were accomplished using PCR to generate the appropriate DNA fragment. The 5' end of the PLCγ$_1$ gene was altered to include a new BamHi site and a sequence that would eventually translationally couple the expression of PLCγ to the φ10 gene of the pT5T vector as described by Eisenberg, S. P., Evans, R. J., Arend, W. P., Verderber, E., Brewer, M. T., Hannum, C. H., & Thompson, R. C. (1990) *Nature(London)* 343,341–346.

Primers 01 and 02 were used to generate a 508 bp fragment (from template DNA pPLC 1 ) containing a 5' BamHI site and 3' EcoRI site. This new restriction fragment was substituted for the analogous fragment in pPLC1 to produce pPLC2.

PCR-mediated mutagenesis with template pPLC2 and with primers 03–05 to generate one mutant fragment and primers 04–06 to generate the second mutant fragment was used to restructure the 3' end, to add DNA sequence encoding the epitope tag Glu-Glu-Phe (which is recognized by the monoclonal antibody YL1/2) (Kilmartin, J. V., Wright, B., & Milstein, C. (1982) *J. Cell. Biol.* 93,576–582), and to change the tandem AGG—AGG codons to CGG—CGG at amino acid positions 944– 945 and 1279–1280. Tandem AGG codons are associated with poor protein expression in *E. coli* (Bonekamp, F., & Jensen, K. (1988) *Nucl. Acids Res.* 17, 3013–3024).

Using the isolated mutant fragments from each of these PCRs together as template, the final PCR was carried out using primers 03–06 which yielded, after restriction enzyme digestion, a SphI and HindIII fragment which was used to replace the analogous fragment in pPLC2. The resulting plasmid, pPLC3, contained the coding sequence of the $PLC\gamma_1$ gene on a BamHI-HindIII fragment with both the sequence encoding the Glu-Glu-Phe tag at the 3' end as well as the changed AGG codons. FIG. 3 shows the final cDNA sequence encoding the enzyme and its epitope tag. (SEQ.ID.NO.: 3) Finally, the BamHI-HindIII fragment from pPLC3 was transferred into the BamHI-HindIII site of pTST, generating pTST-PLC4. This construct was used to produce $PLC\gamma_1$ (containing the Glu-Glu-Phe epitope tag at the C-terminus) translationally coupled to the expression of φ10 protein in the pT5T vector.

Expression and Purification of $PLC\gamma_1$. To express $PLC\gamma_1$ the plasmid pT5T-PLC4 was transformed into *E. coli* BL21 (DE3). The transformed cells were grown in LB media containing ampicillin (100 µg/ml) and tetracycline (12.5 µg/ml) at 20° C. until the optical density of the cultures at 550 nm was equal to 0.8. This transformed bacterial cell has been deposited with the ATCC and has been assigned the number ATCC 69421. Expression of $PLC\gamma_1$ was then induced by addition of isopropyl β-D-thiogalactopyranoside (0.5 mM final concentration) to the cultures. After growing for another 6 hours the cells were harvested and $PLC\gamma_1$ was purified as described below. $PLC\gamma_1$ was isolated from *E. coli* by resuspending a cell pellet in standard buffer, 50 mM Tris-Cl pH 8.0, 2 mM $MgCl_2$, 10 mM $CaCl_2$, 1 mM EGTA, 5 mM DTT, 5 mM streptomycin sulfate, 1 mM PMSF, 2 µg/ml leupeptin, 2 µg/ml antipain, 10 µg/ml aprotinin (approximately 5 g wet packed cells/ 10 ml buffer). The resuspended cells were broken by sonication and the cell debris pelleted by centrifugation at 30,000×g at 4° C. for 30 minutes. The soluble fraction was applied at a flow rate of approximately 0.5 ml/min. to a 2 ml column of the monoclonal antibody YL 1/2(4 mg antibody/ml resin) coupled to cyanogen bromide activated Sepharose. The YL1/2 Sepharose column, which binds the epitope tag Glu-Glu-Phe had previously been equilibrated with standard buffer. After loading the protein onto the column, the column was washed with standard buffer (100 mls) $PLC\gamma_1$ was eluted with 3×5ml 5 mM Asp-Phe dipeptide (Sigma) in standard buffer. The column was regenerated by washing with phosphate buffered saline (PBS)+2 M NaCl and then stored in PBS +0.02% $NaN_3$ (wt./vol). The $PLC\gamma_1$ was obtained in >80% purity and in a 0.05 to 0.5% yield based on the total starting soluble *E. coli* protein. In some cases the $PLC\gamma_1$ was further purified. This is not necessary for routine drag screening. To further purify the $PLC\gamma_1$ the protein eluted from the YL1/2 column was chromatographed by HPLC on a MonoQ HR10-10 column (Pharmacia) where buffer A was standard buffer and buffer B was standard buffer +1M KCl. The column was mn at 1 ml/min. and the gradient was 0–30% B in 40 min., 30–50% B in 50 min., 50–100% "B" in 70 min. $PLC\gamma_1$ eluted at approximately 25–30% B.

Assay of purified $PLC\gamma_1$ activity. Activity of the purified $PLC\gamma_1$ was assayed at 30° C. Reactions were never allowed to proceed to more than 10% completion based on the limiting substrate. A typical reaction contained the following: 50 mM HEPES pH7.5, 0.1% Deoxycholate, 3 mM $CACl_2$, 1 mM EGTA, 0.1 mM DTT with phosphatidyl inositol (1–1000 µM) (PI) and 0.02 µCi [$^3H$]-phosphatidyl inositol (PI) as substrate. The phospholipid components were dried under a gentle stream of nitrogen and resuspended in assay buffer. The substrate mix is then vortexed and sonicated (10 sec. with probe sonicator) to disperse the lipid and form micelies. After thermally preequilibrating the assay mixture in the absence of enzyme, the reaction was initiated by adding $PLC\gamma_1$. Reactions containing 0.2 ml aliquots were terminated by addition of ¼ volume 1 N HCl, 5 mM EGTA and transferred to an ice bath. The quenched reactions are then filtered through a Q Sepharose (Pharmacia) column. To prepare the Q Sepharose column 1 ml of Q Sepharose slurry is added to a disposable plastic column. The resin is equilibrated by passing through 20 ml of 10 mM $NH_4H_2PO_4$, pH 3.5. The quenched reaction, typically 200 µl, is applied to the column and 3 ml of 10 mM $NH_4H_2PO_4$, pH 3.5 is added, the flow through from this step is collected in a scintillation vial, mixed with 10 ml of scintillation fluid and counted in a Beckman LS3801 scintillation counter.

The activity of the bacterially expressed $PLC\gamma_1$ determined as described hereinabove was compared with the activity in the same assay of naturally derived bovine brain PLCγ. The bovine brain PLCγ was purified to approximately 80% homogeneity by modification of a previously described protocol (S. H. Ryu et al. *J. Biol. Chem.*, 262:12511– 12518 (1987)) in which the chromatography was carded out at 4° C. through three steps: DEAE-Cellulose followed by reverse-phase chromatography on a Bio-Gel phenyl 5-PW (Biorad) column and final purification on a Mono-Q column (Pharmacia). The bacterially expressed $PLC\gamma_1$ had a specific activity of 13.8 µmol/min/mg compared with a specific activity of 11.4 µmol/min/mg for the naturally derived bovine brain PLCγ.

Assay of Inhibitory Activity of Compounds

The inhibitory activity of certain compounds against $PLC\gamma_1$ was assessed by including known concentrations of the compound in the assay mixture described above prior to the addition of the enzyme. The relative inhibitory concentrations calculated from the assay are shown in Tables 1 and 2.

TABLE 1

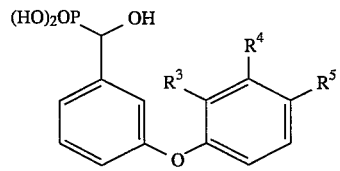

| $R^3$ | $R^4$ | $R^5$ | $IC_{50}$ (µM) |
|---|---|---|---|
| H | —Cl | H | 10 |
| H | H | H | 190 |
| H | —Cl | —Cl | 56 |
| H | H | —Cl | 36 |
| —Cl | H | H | 17 |
| H | H | —$OCH_3$ | 7 |
| H | H | —$CH_3$ | 13 |
| H | H | —OH | 3 |

TABLE 2

[Structure: HO-CH(OP(OH)₂)-C₆H₄-O-C₆H₂(R³)(R⁴)(R⁵)]

| R³ | R⁴ | R⁵ | IC₅₀ (μM) |
|---|---|---|---|
| H | —Cl | H | 5 |
| H | —CH₂CH₃ | H | 37 |

TABLE 2-continued

[Structure: HO-CH(OP(OH)₂)-C₆H₄-O-C₆H₂(R³)(R⁴)(R⁵)]

| R³ | R⁴ | R⁵ | IC₅₀ (μM) |
|---|---|---|---|
| H | —OCH₃ | H | 8 |

What is claimed is:

1. A method of expressing and isolating mammalian phospholipase $C\gamma_1$ in an enzymatically active form which comprises the steps of:

a) transforming bacterial host cells with a plasmid that comprises a cDNA which encodes said mammalian phospholipase $C\gamma_1$, wherein the cDNA has the nucleotide sequence of SEQ.ID.NO.: 1, and a second cDNA operationally linked to the cDNA of SEQ.ID.NO.: 1, said second cDNA which encodes for the epitope tag GluGluPhe, said epitope tag which is incorporated at the C-terminus of the phospholipase $C\gamma_1$ when it is expressed;

b) growing and harvesting the transformed host cells;

c) exposing the harvested host cells to an affinity column containing an antibody which specifically binds said epitope tag; and d) eluting said affinity column to provide isolated enzymatically active mammalian phospholipase $C\gamma_1$.

* * * * *

UNITED STATES PATENT AND TRADEMARK OFFICE
CERTIFICATE OF CORRECTION

PATENT NO. : 5,474,921
DATED : Dec. 12, 1995
INVENTOR(S) : Kenneth S. Koblan, et al It is certified that error appears in the above-indentified patent and that said Letters Patent is hereby corrected as shown below:

At Column 25, lines 33-35 in Claim 1, please replace the term "eDNA" with -- cDNA -- (three instances).

Signed and Sealed this

Twenty-third Day of April, 1996

Attest:

BRUCE LEHMAN

*Attesting Officer*  Commissioner of Patents and Trademarks